(12) United States Patent
Han

(10) Patent No.: US 8,214,162 B2
(45) Date of Patent: Jul. 3, 2012

(54) ESTIMATION OF NON-EQUIBIAXIAL STRESS USING INSTRUMENTED INDENTATION TECHNIQUE

(75) Inventor: Jae Hwan Han, Seoul (KR)

(73) Assignee: Frontics, Inc. (KR)

( * ) Notice: Subject to any disclaimer, the term of this patent is extended or adjusted under 35 U.S.C. 154(b) by 382 days.

(21) Appl. No.: 12/526,166

(22) PCT Filed: Feb. 6, 2007

(86) PCT No.: PCT/KR2007/000621
§ 371 (c)(1),
(2), (4) Date: Aug. 6, 2009

(87) PCT Pub. No.: WO2008/096914
PCT Pub. Date: Aug. 14, 2008

(65) Prior Publication Data
US 2010/0198530 A1    Aug. 5, 2010

(51) Int. Cl.
*G01N 3/08* (2006.01)
(52) U.S. Cl. .............. 702/43; 702/33; 702/42; 73/81; 73/823; 73/789; 73/804; 73/799; 356/32; 356/35.5
(58) Field of Classification Search ............... 702/33, 702/42, 43; 73/81, 823, 861, 789, 804, 799, 73/826; 356/32, 35.5, 432, 496, 626
See application file for complete search history.

(56) References Cited

U.S. PATENT DOCUMENTS

| | | | | |
|---|---|---|---|---|
| 5,003,982 A * | 4/1991 | Halperin | | 600/508 |
| 5,146,779 A * | 9/1992 | Sugimoto et al. | | 73/81 |
| 5,432,595 A * | 7/1995 | Pechersky | | 356/35.5 |
| 5,433,215 A * | 7/1995 | Athanasiou et al. | | 600/587 |
| 6,134,954 A * | 10/2000 | Suresh et al. | | 73/81 |
| 6,155,104 A * | 12/2000 | Suresh et al. | | 73/81 |
| 6,247,355 B1 * | 6/2001 | Suresh et al. | | 73/82 |
| 6,311,135 B1 * | 10/2001 | Suresh et al. | | 702/43 |
| 6,470,756 B1 * | 10/2002 | Prime | | 73/799 |
| 6,568,250 B1 * | 5/2003 | Sinha | | 73/81 |
| 6,851,300 B2 | 2/2005 | Kwon et al. | | |
| 7,165,463 B2 * | 1/2007 | Liu et al. | | 73/861 |
| 7,472,603 B2 * | 1/2009 | Kim | | 73/823 |
| 7,487,051 B2 * | 2/2009 | Kim et al. | | 702/42 |
| 7,621,173 B2 * | 11/2009 | Hsu et al. | | 73/81 |
| 7,884,924 B2 * | 2/2011 | Numata et al. | | 356/35.5 |
| 2004/0020276 A1 | 2/2004 | Kwon et al. | | |
| 2008/0141782 A1 * | 6/2008 | Kim | | 73/823 |

FOREIGN PATENT DOCUMENTS
WO    WO-2006/071001 A1    7/2006
* cited by examiner

*Primary Examiner* — Carol Tsai
(74) *Attorney, Agent, or Firm* — Harness, Dickey & Pierce, P.L.C.

(57) ABSTRACT

Method for evaluating an asymmetric residual stress for a material by the indentation test comprises applying the residual stresses with an uniaxial and an symmetrical biaxial tensions on the material and then performing an instrumented indentation test indenting an asymmetric indenter on the material; and comparing a slope of indentation load-depth curve when the long diagonal direction of the asymmetric indenter is perpendicular to the direction of the largest residual stress with that in stress-free state, and then a slope of indentation load-depth curve when the long diagonal direction of the asymmetric indenter is parallel to the direction of the largest residual stress with that in stress-free state, so as to evaluate the asymmetric residual stress for the material.

21 Claims, 41 Drawing Sheets

[Figure 1]
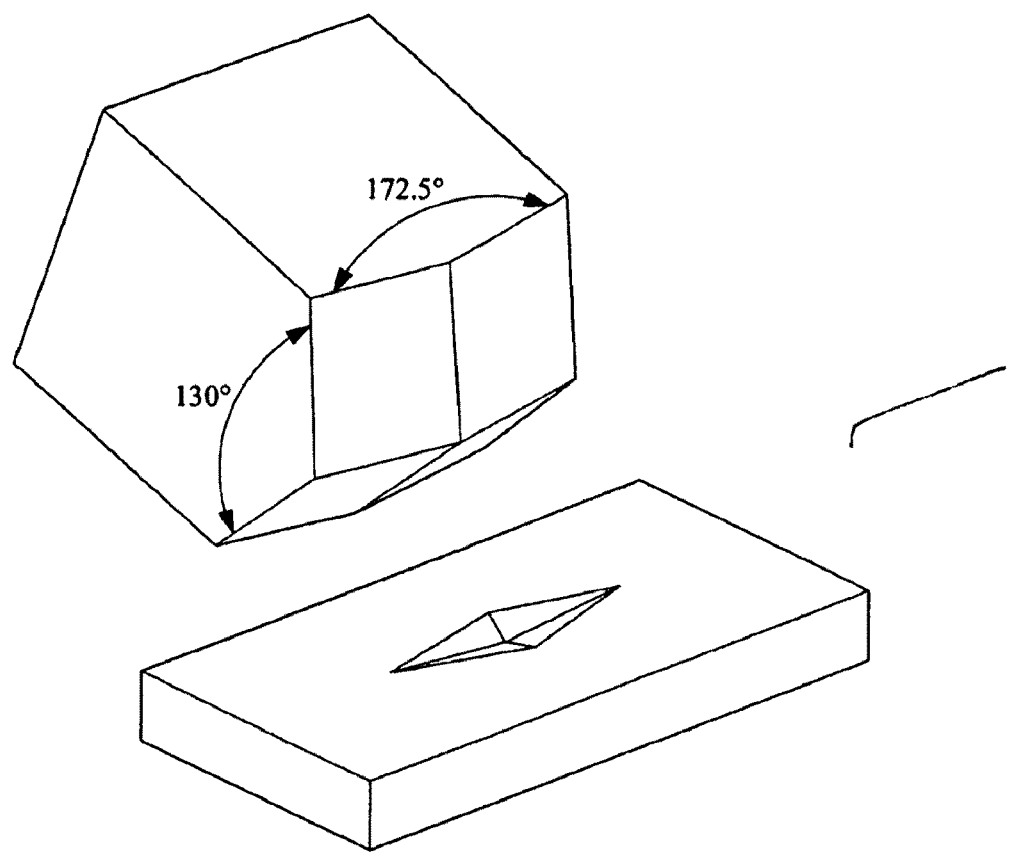

[Figure 2]
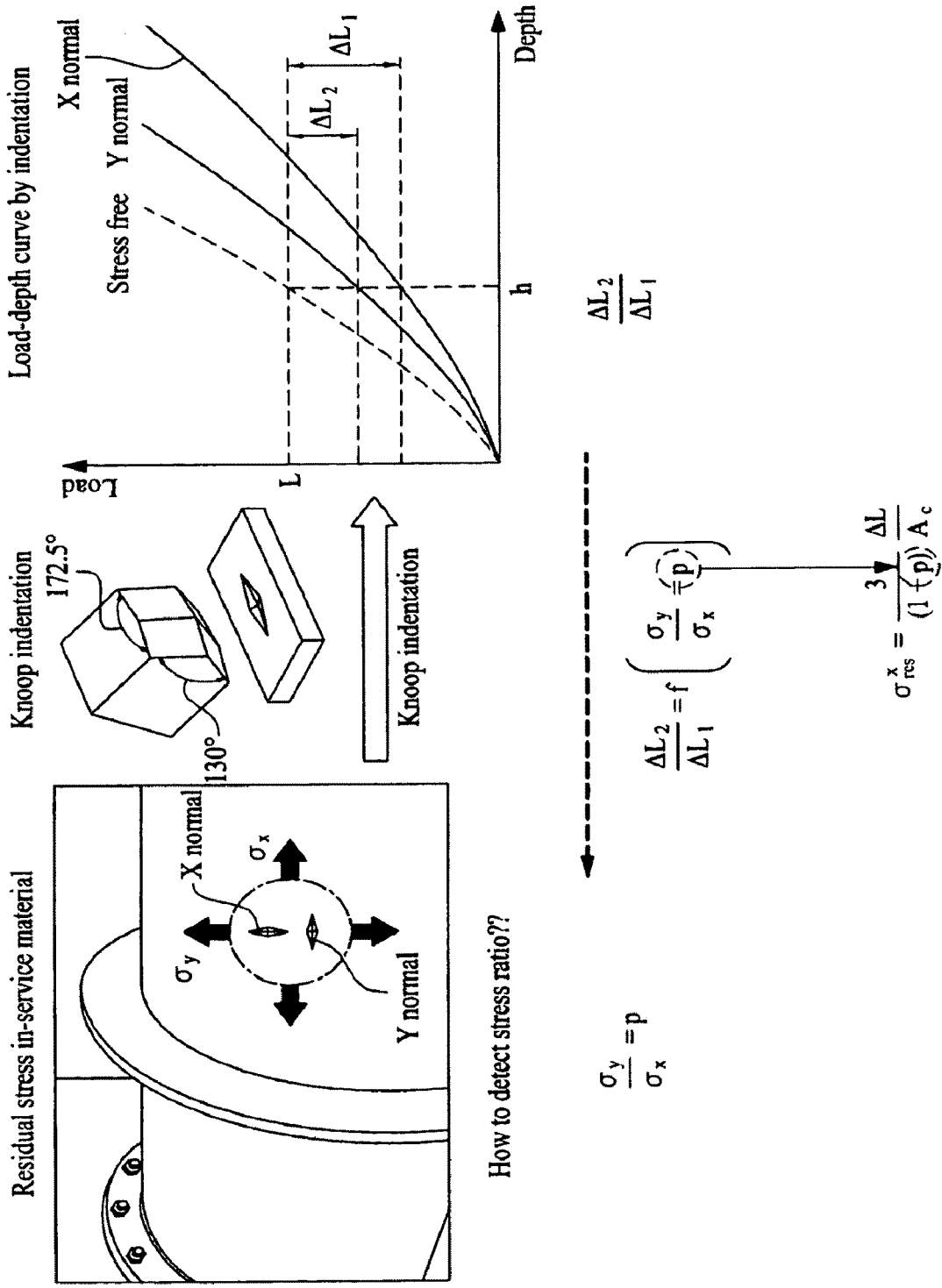

[Figure 3]
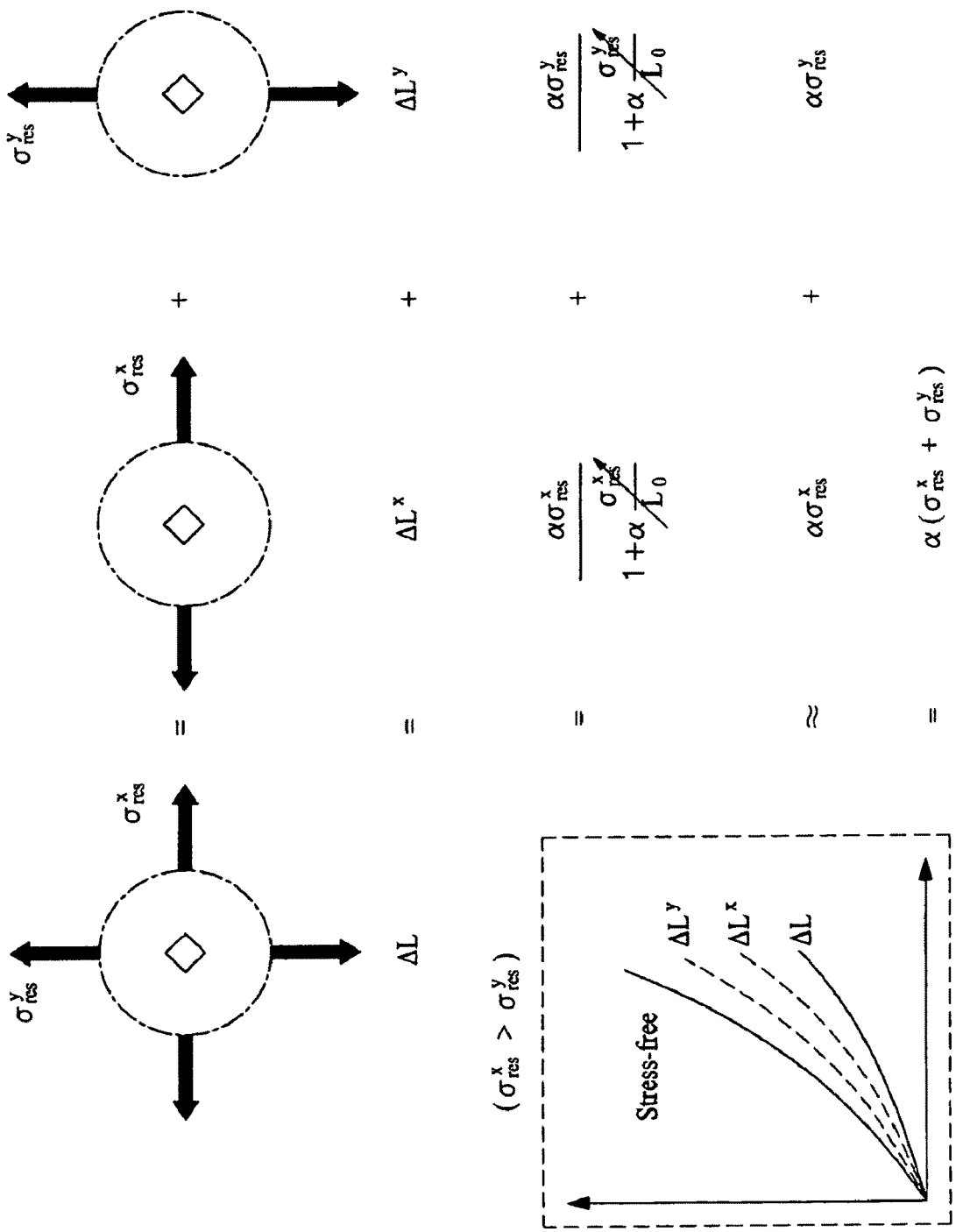

[Figure 4]
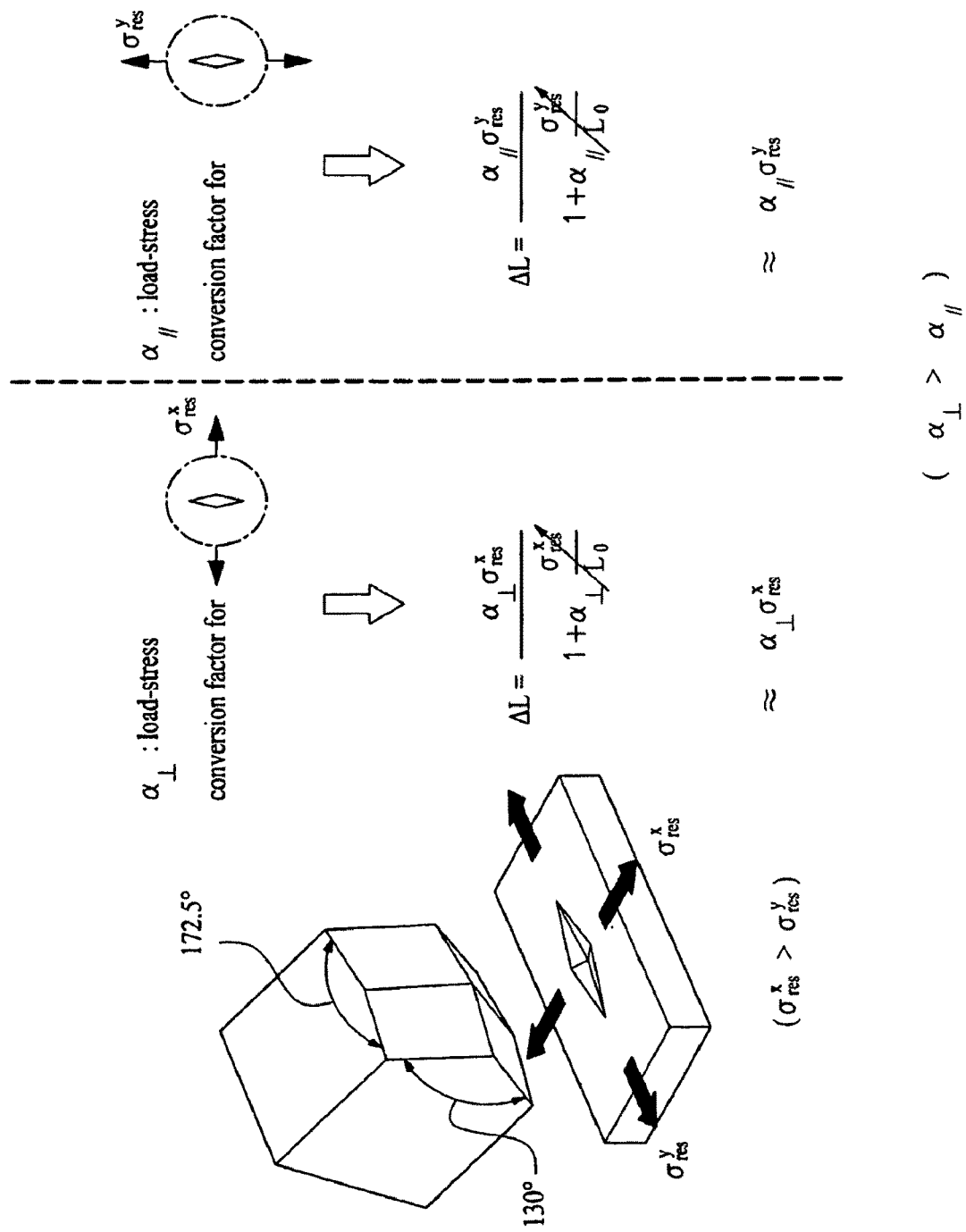

[Figure 5]
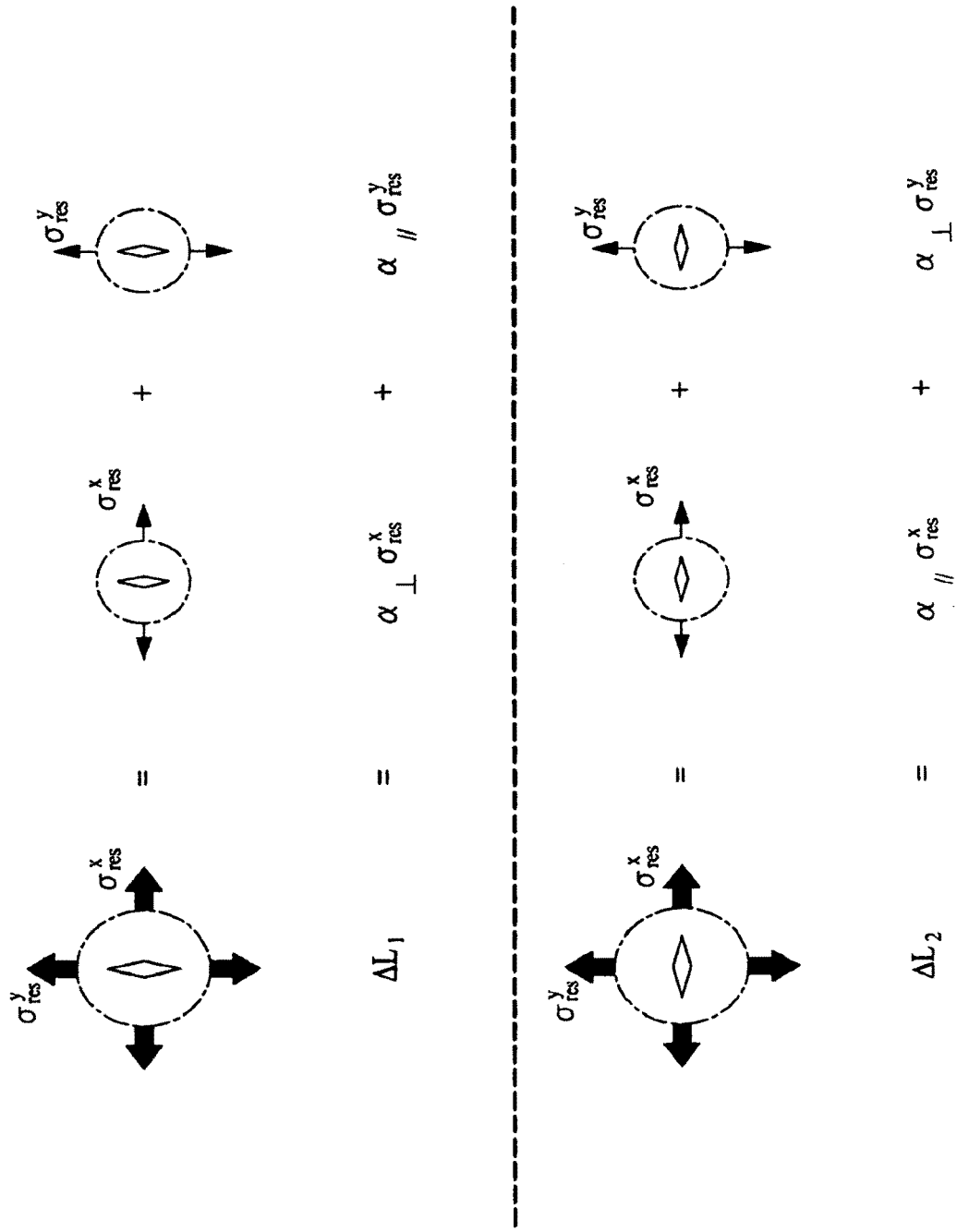

[Figure 6]
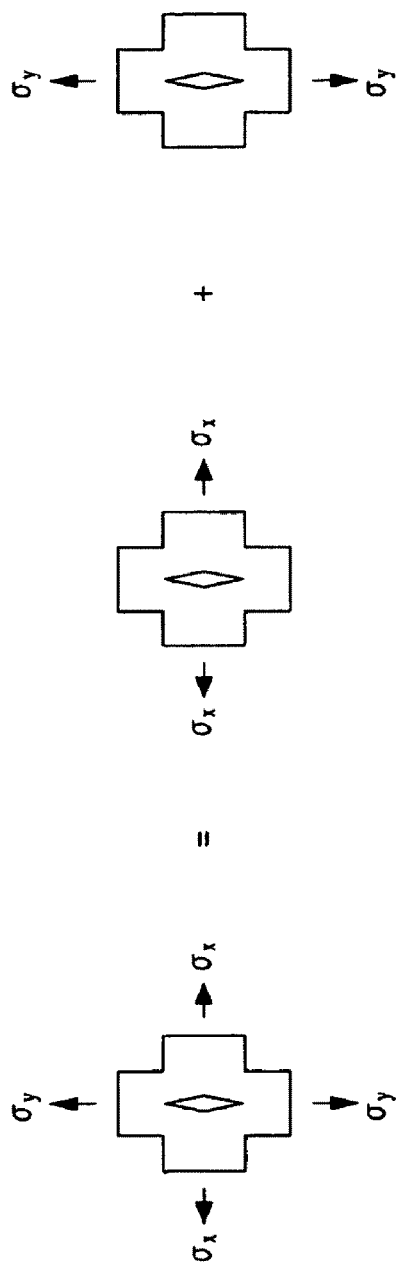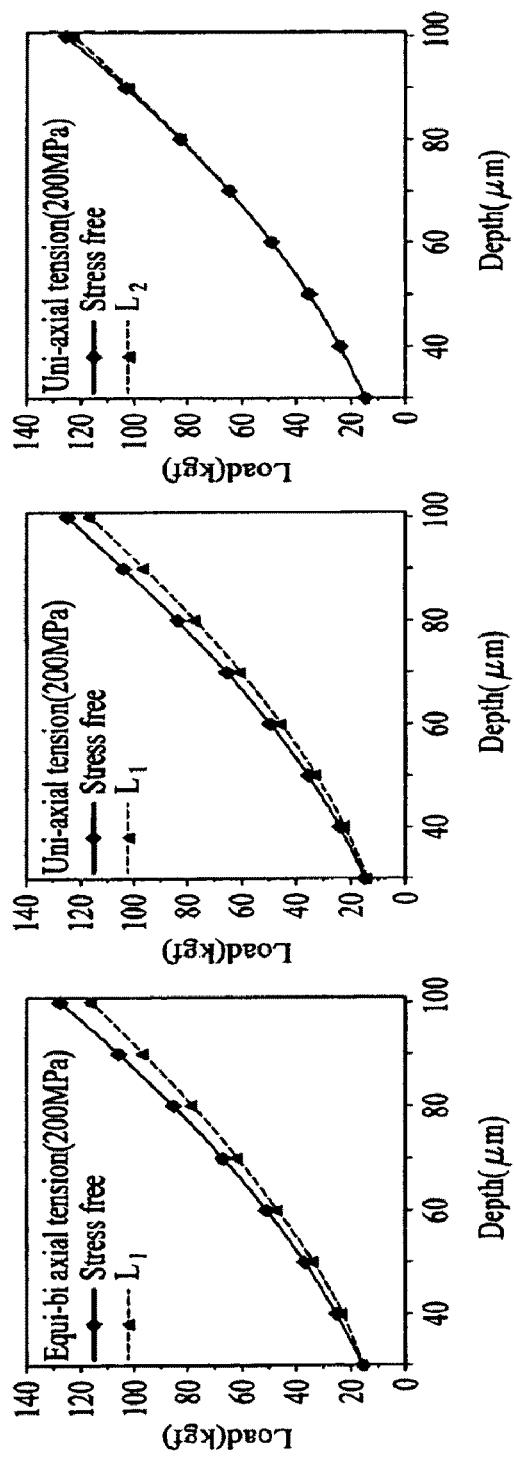

[Figure 7]
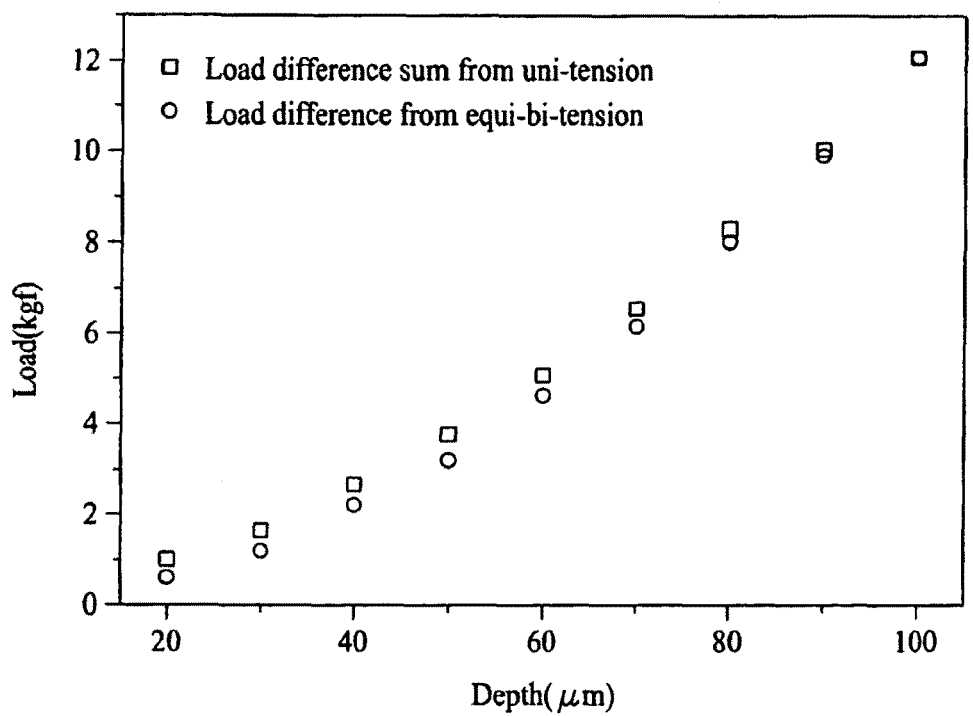

[Figure 8]
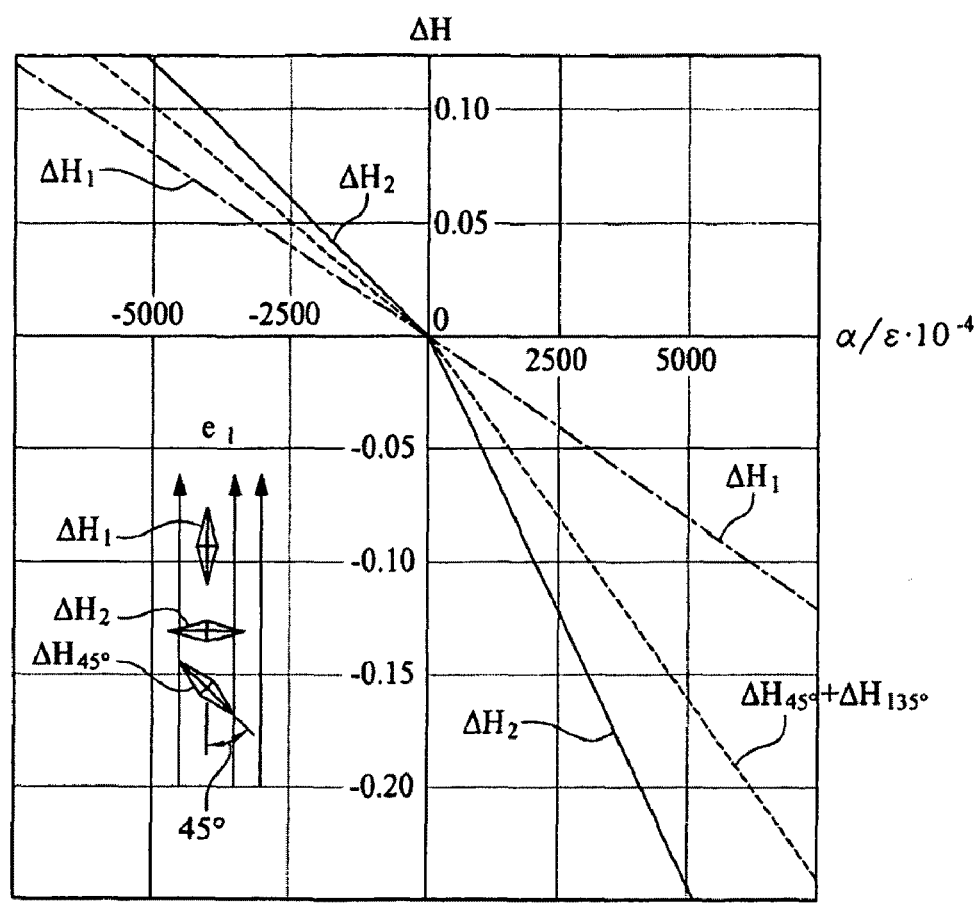

[Figure 9]
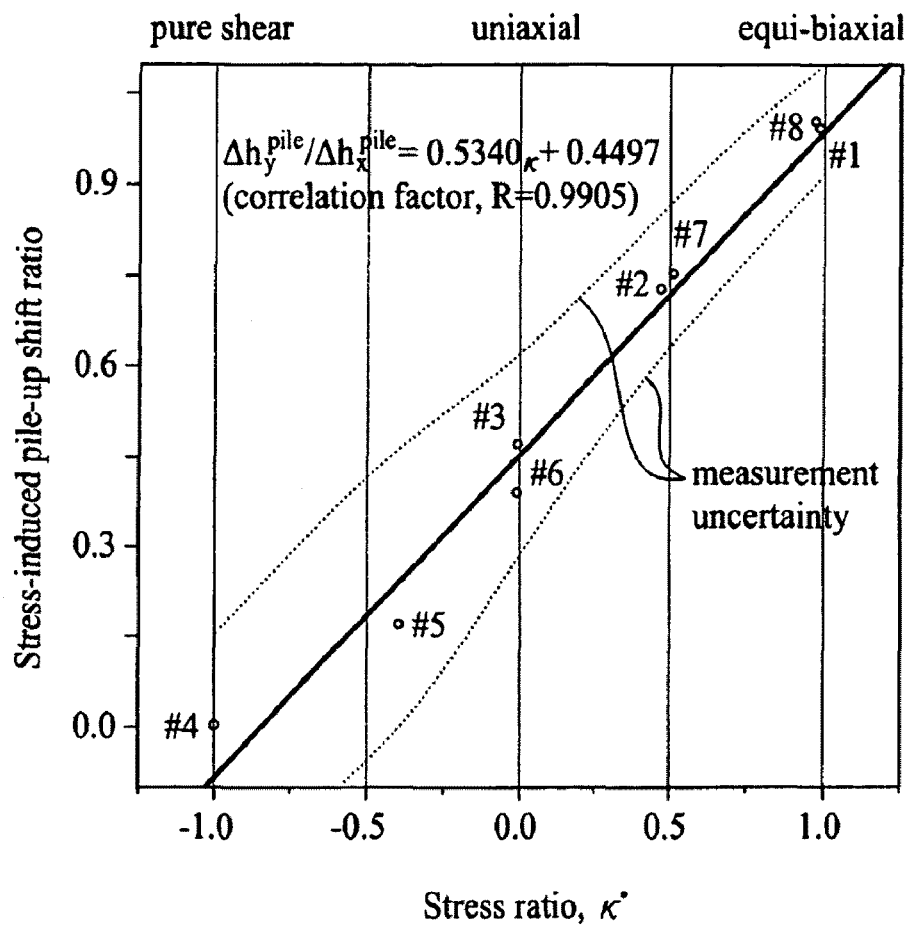

[Figure 10]
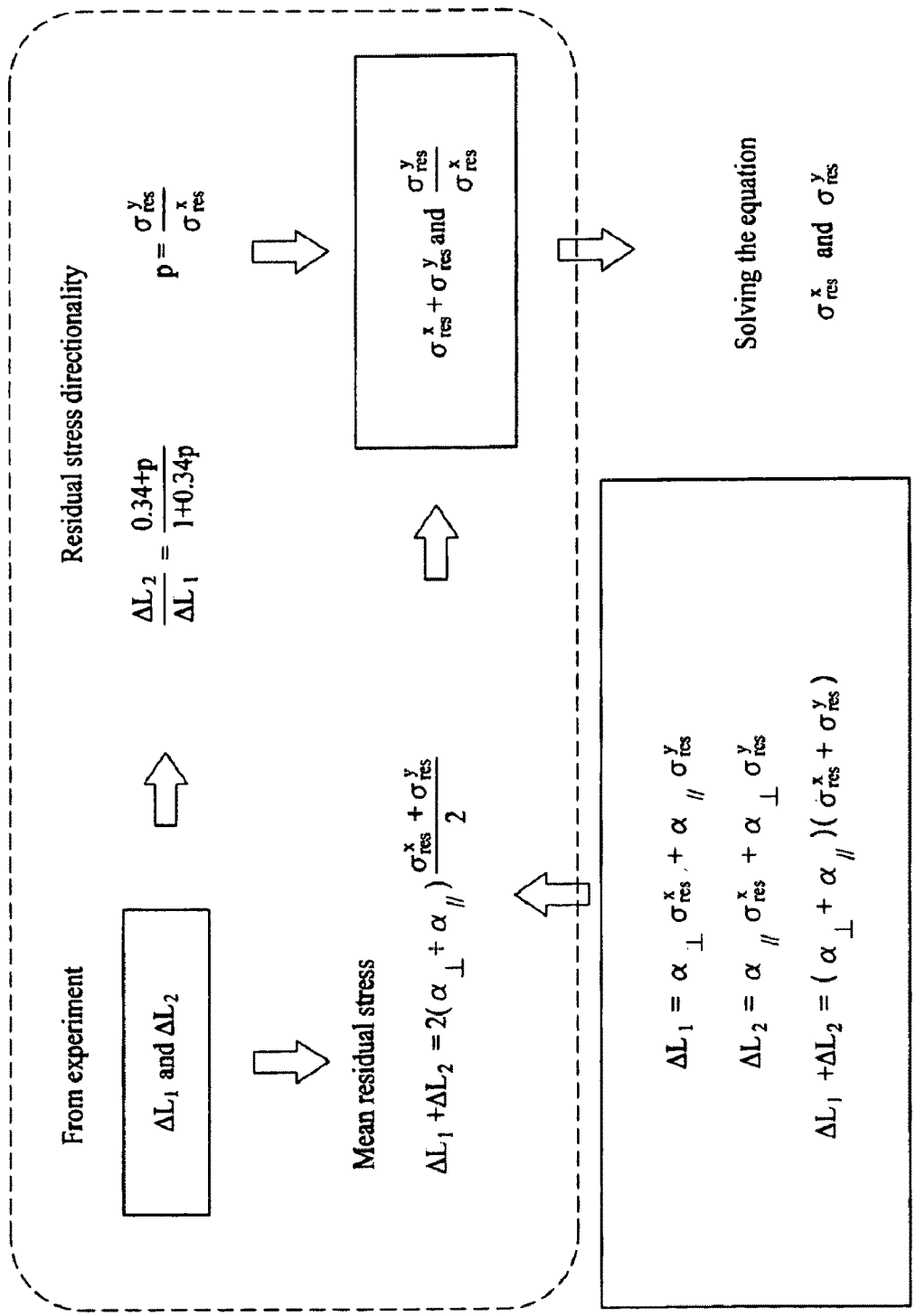

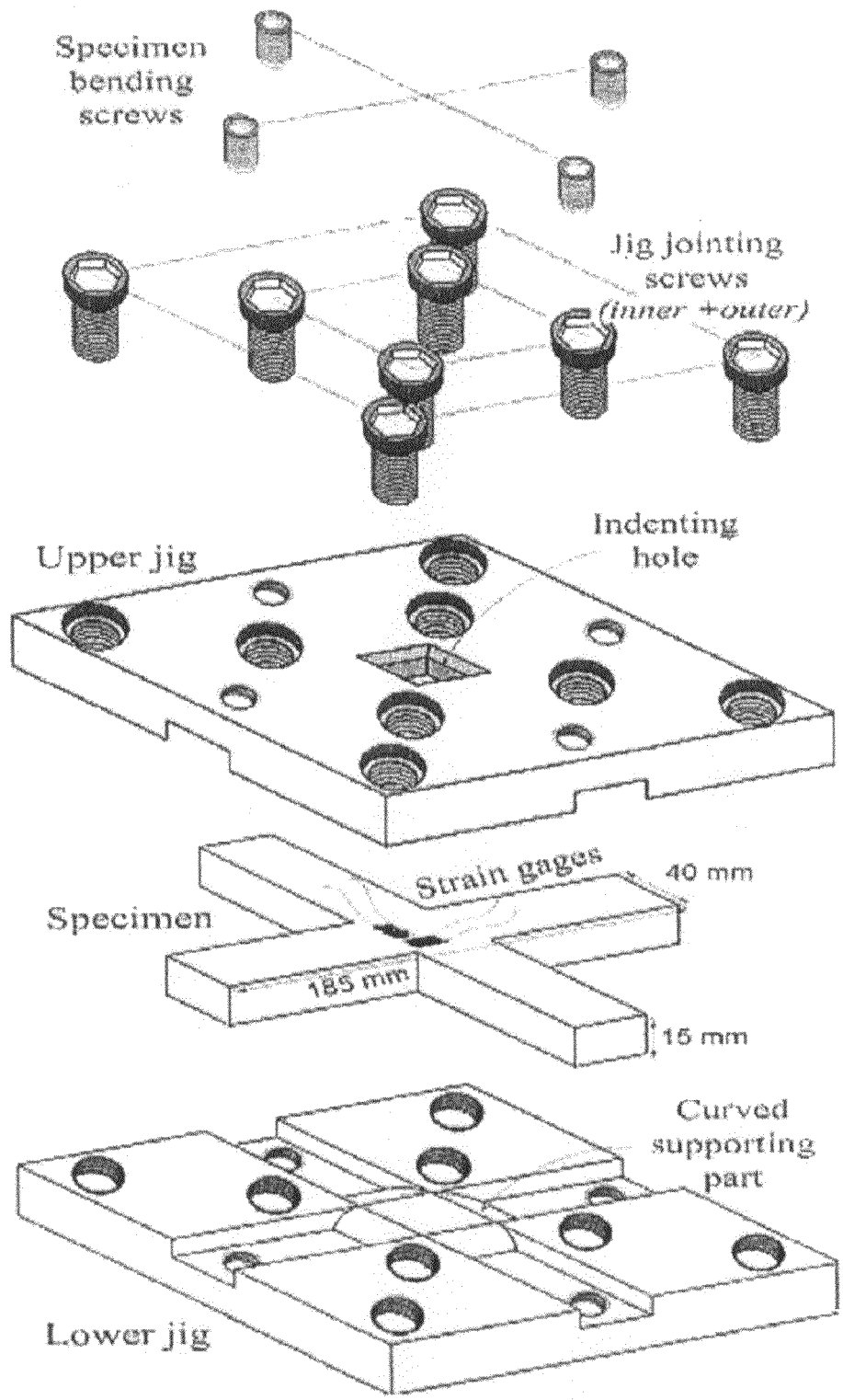
[Figure 11]

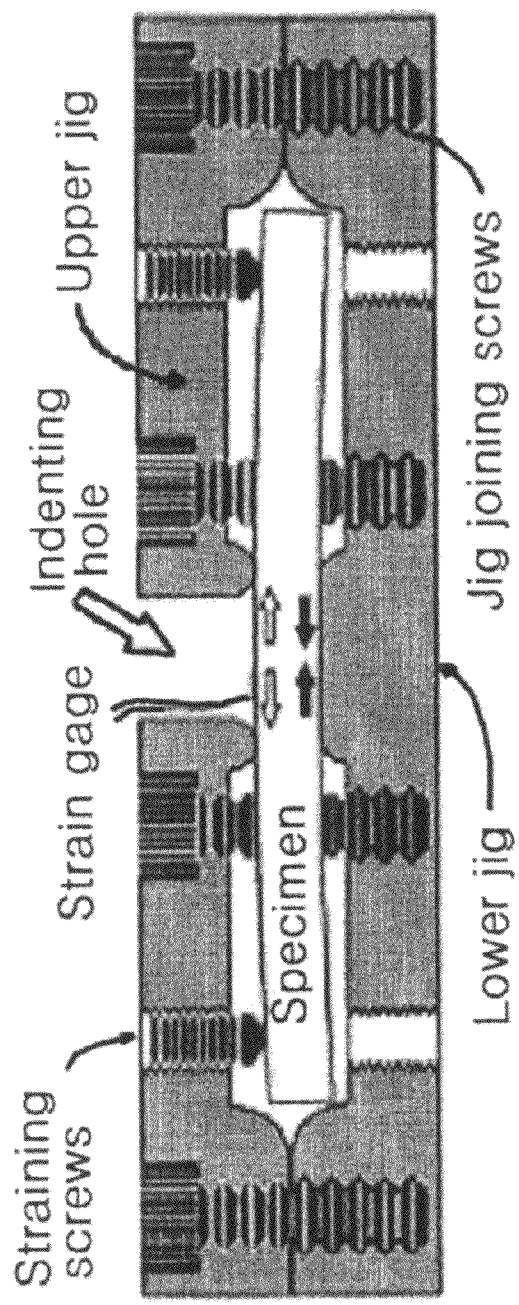
[Figure 12]

[Figure 13]
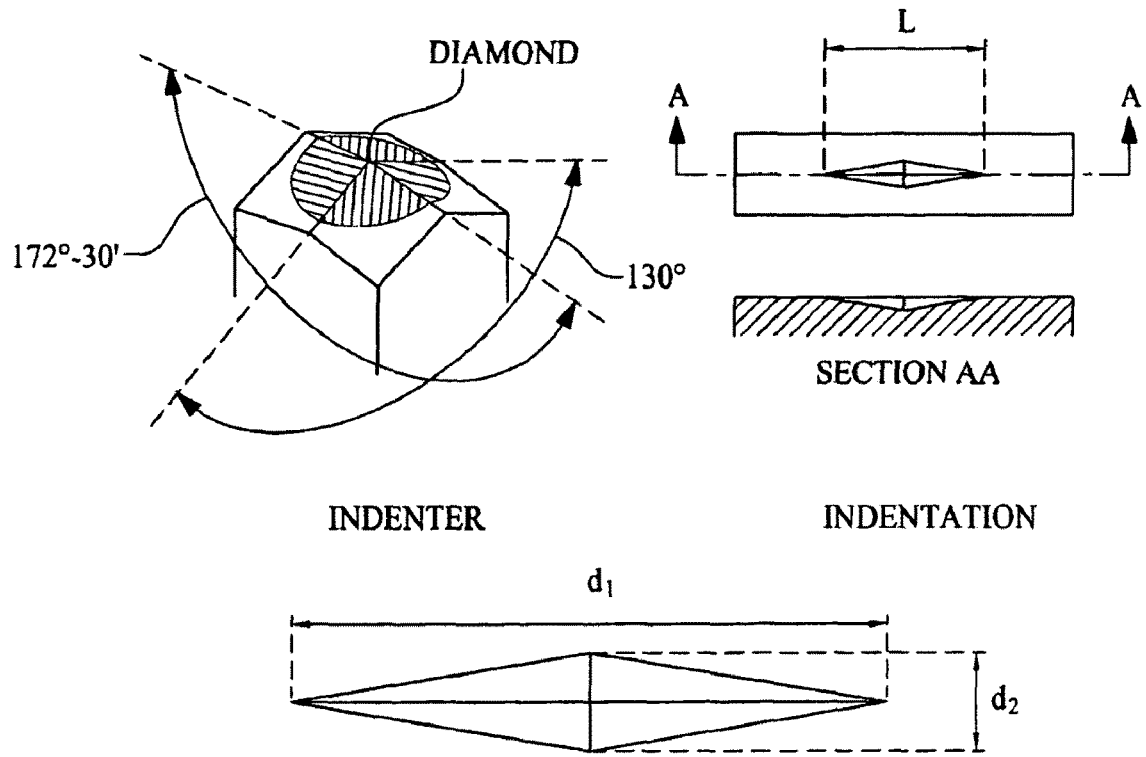
$d_1 : d_2 = 2\tan(172°30'/2) : 2\tan(130°/2) \cong 7.11 : 1$
$$H_K = \frac{14.229P}{d_1^2} \left(kg/mm^2\right)$$

【Figure 14】
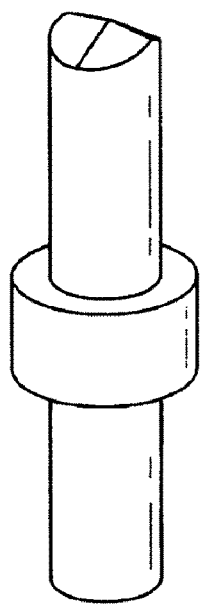

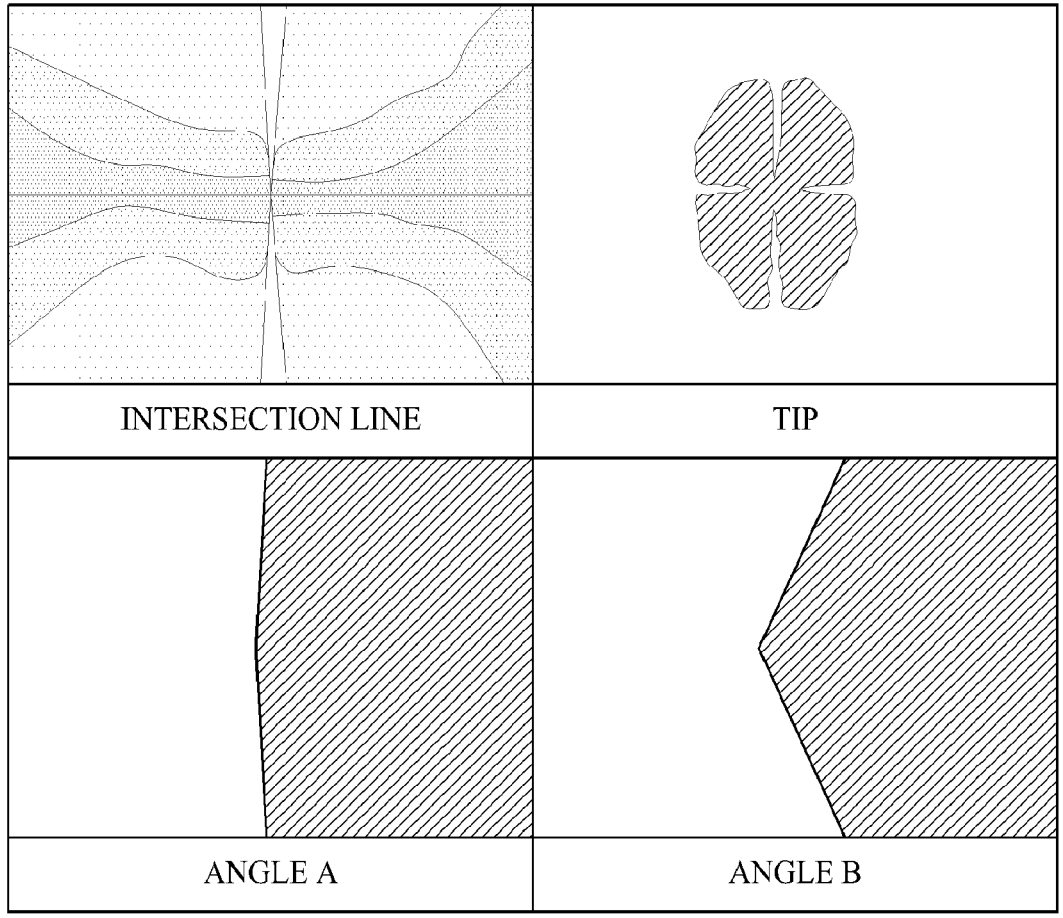
TIP.CORNERS AND SURFACE:            AS TO THE STANDARD
ANGLE A(TOL. 172.50°+/-0.083°):     172.48°
ANGLE B(TOL. 130.00°+/-0.5°):       130.08°
[Figure 15]

[Figure 16]
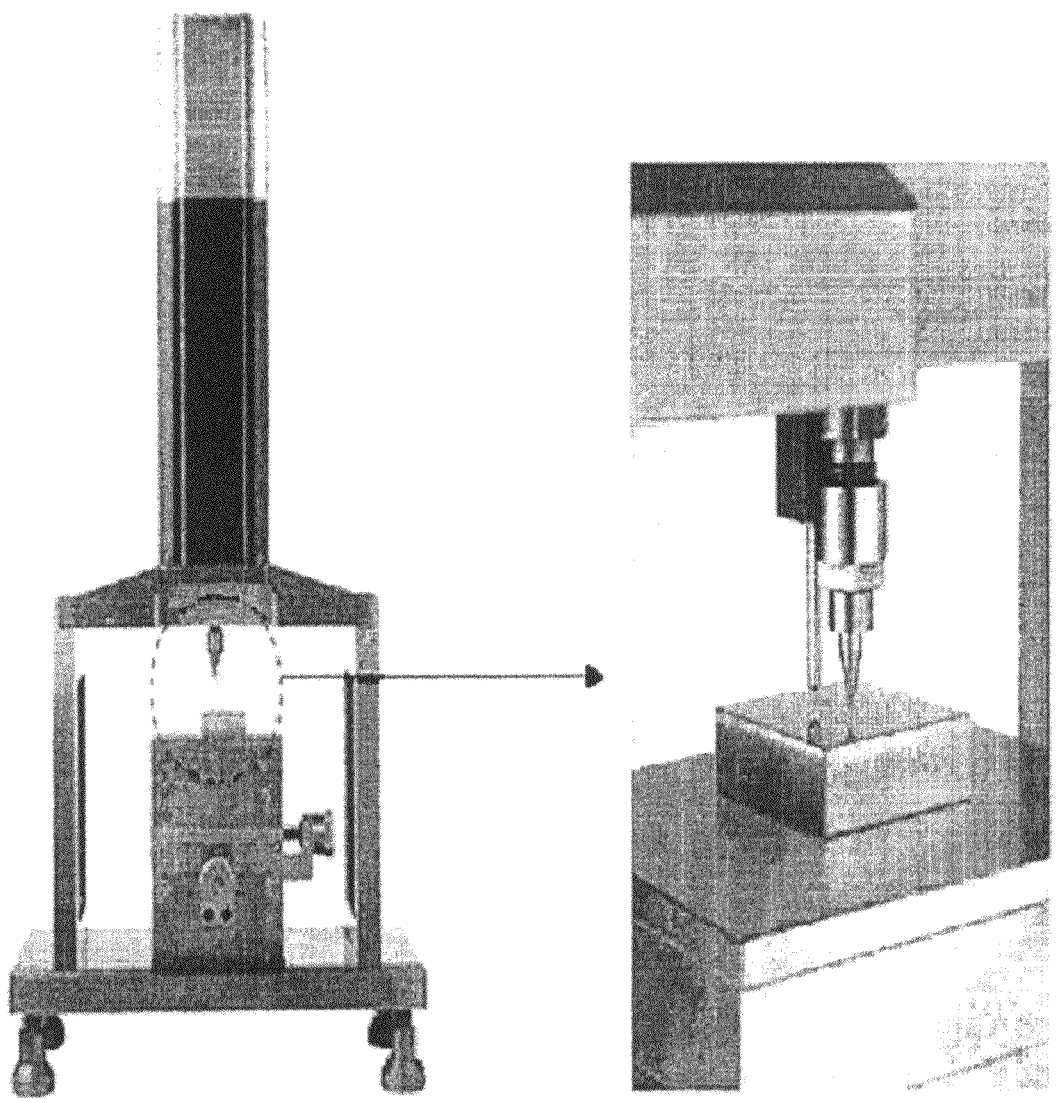

[Figure 17]
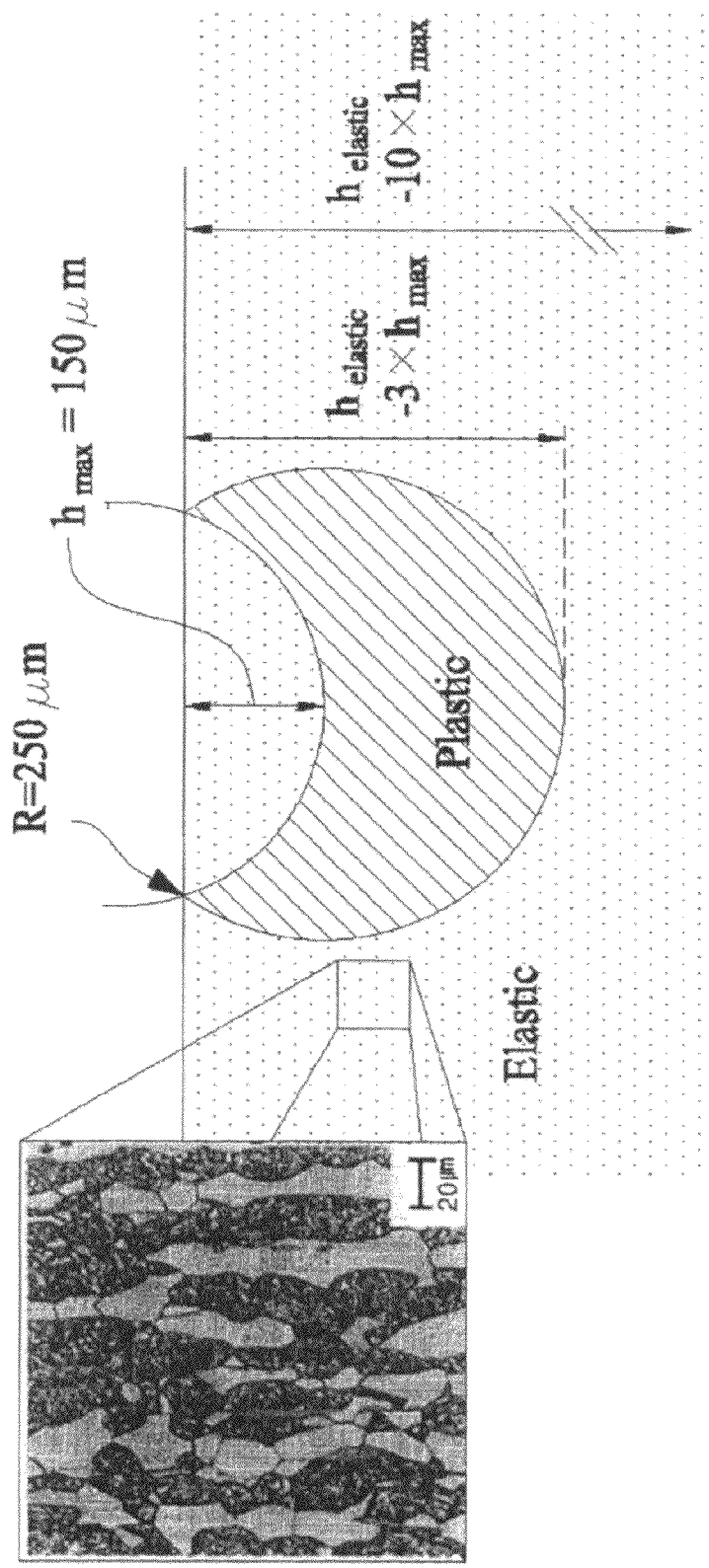

[Figure 18]
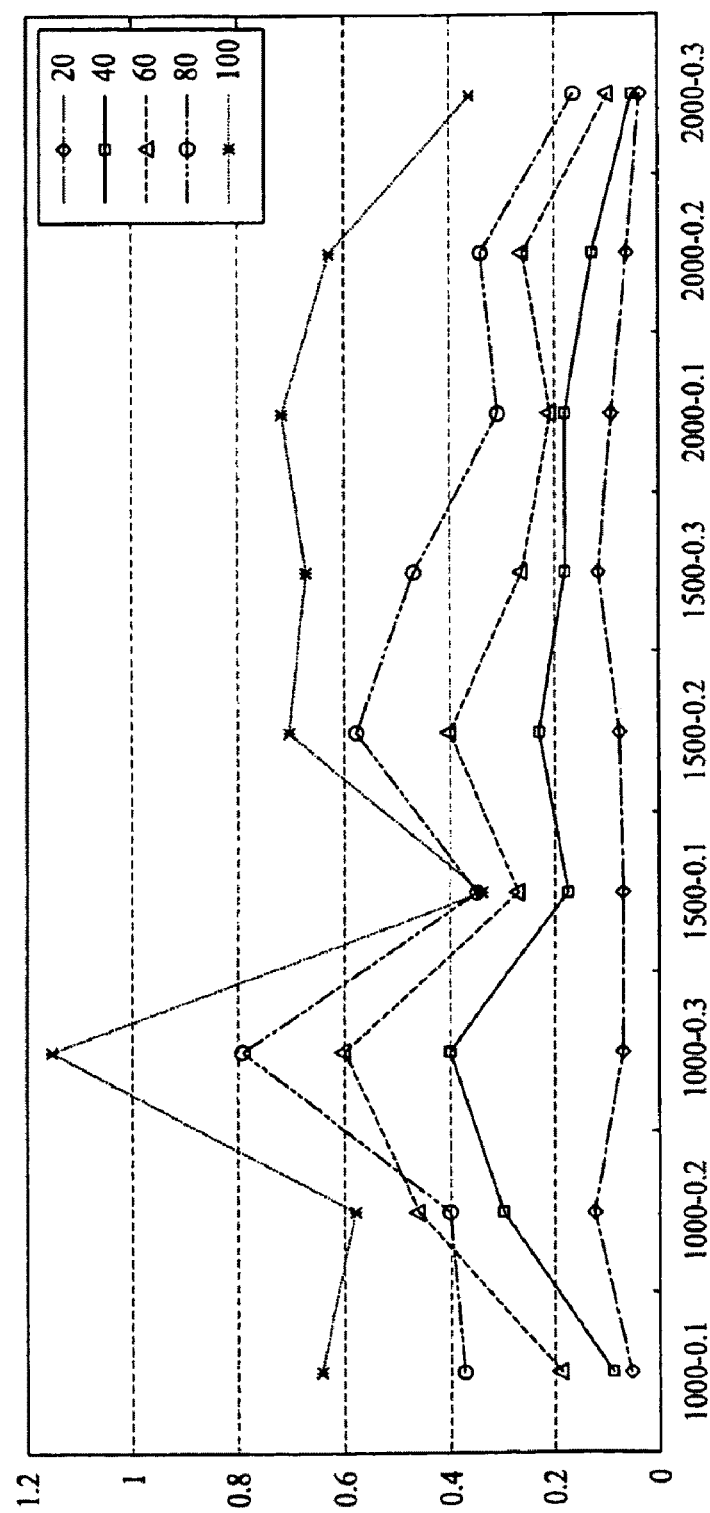

[Figure 19]
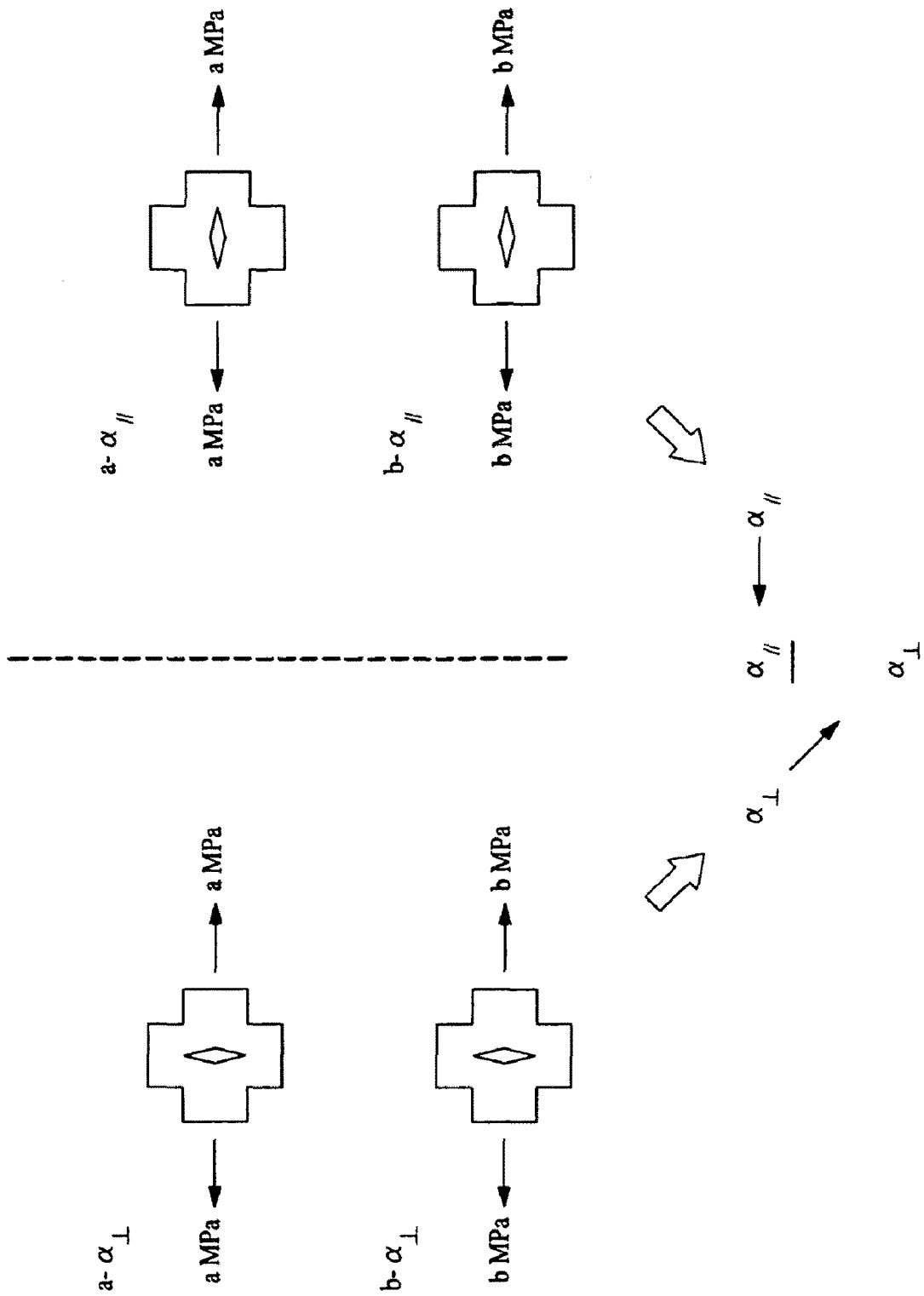

[Figure 20]
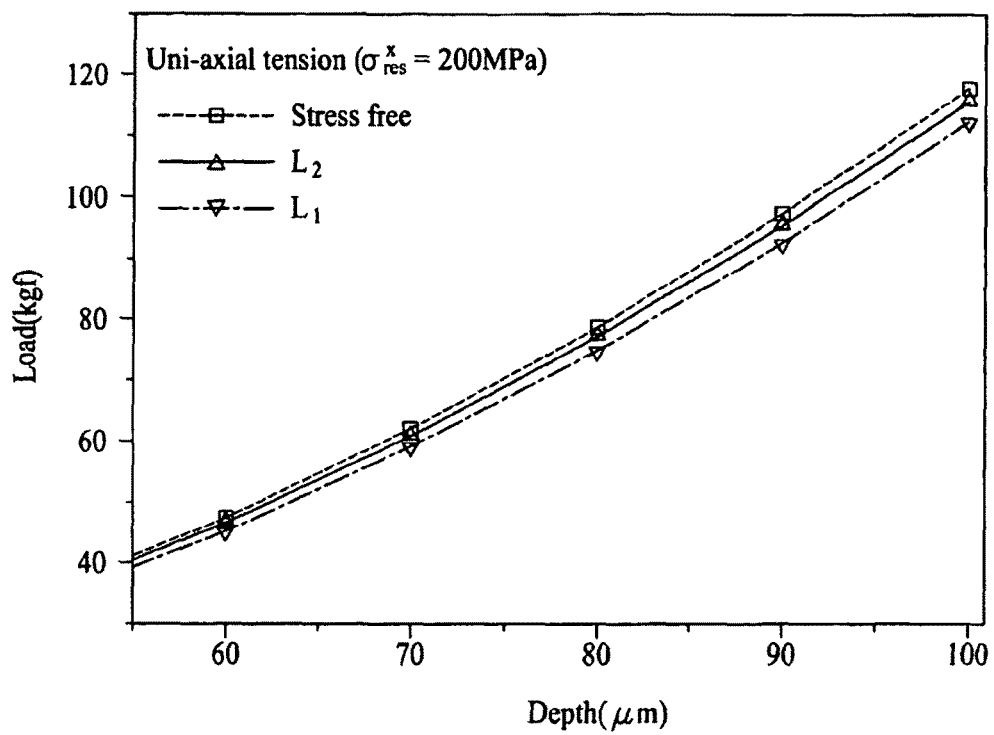

[Figure 21]
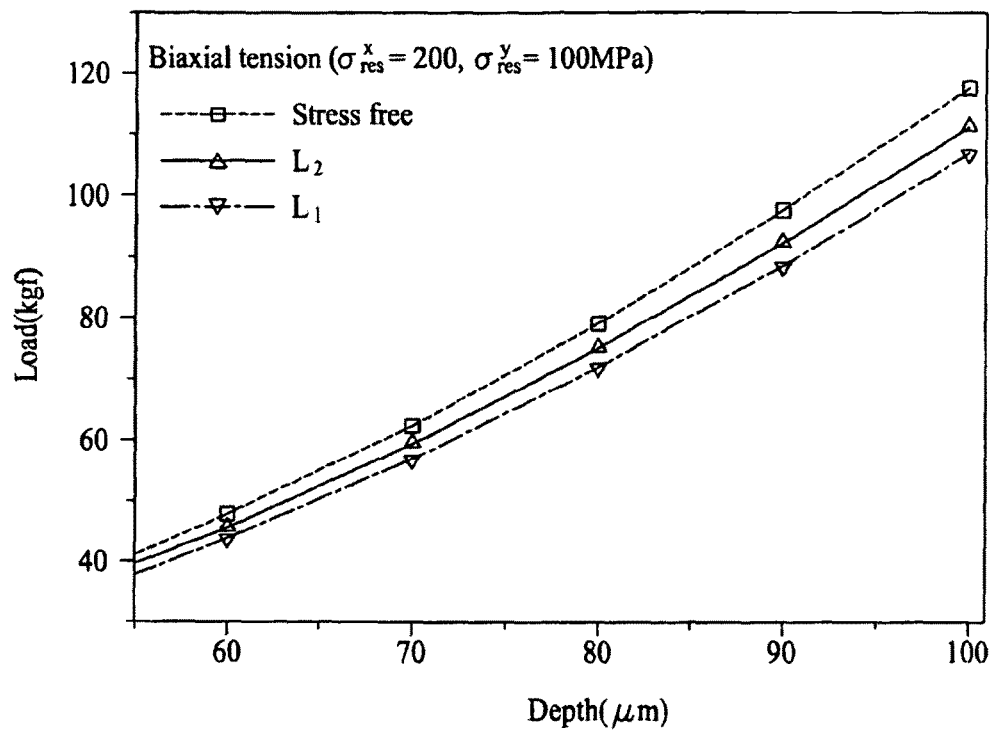

[Figure 22]
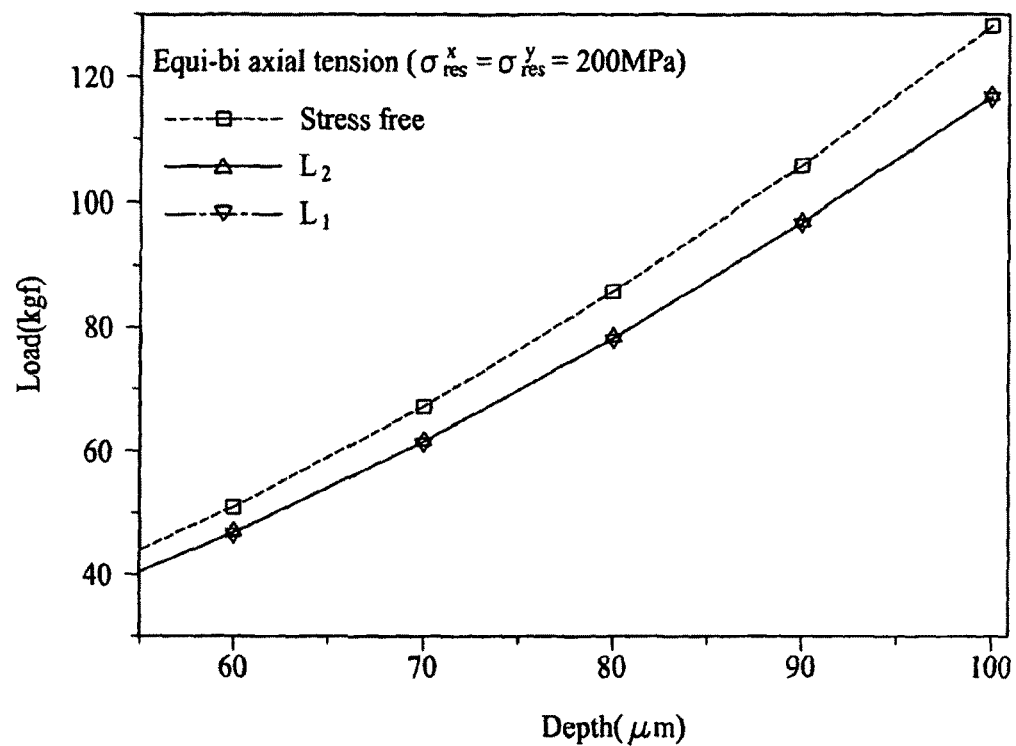

[Figure 23]
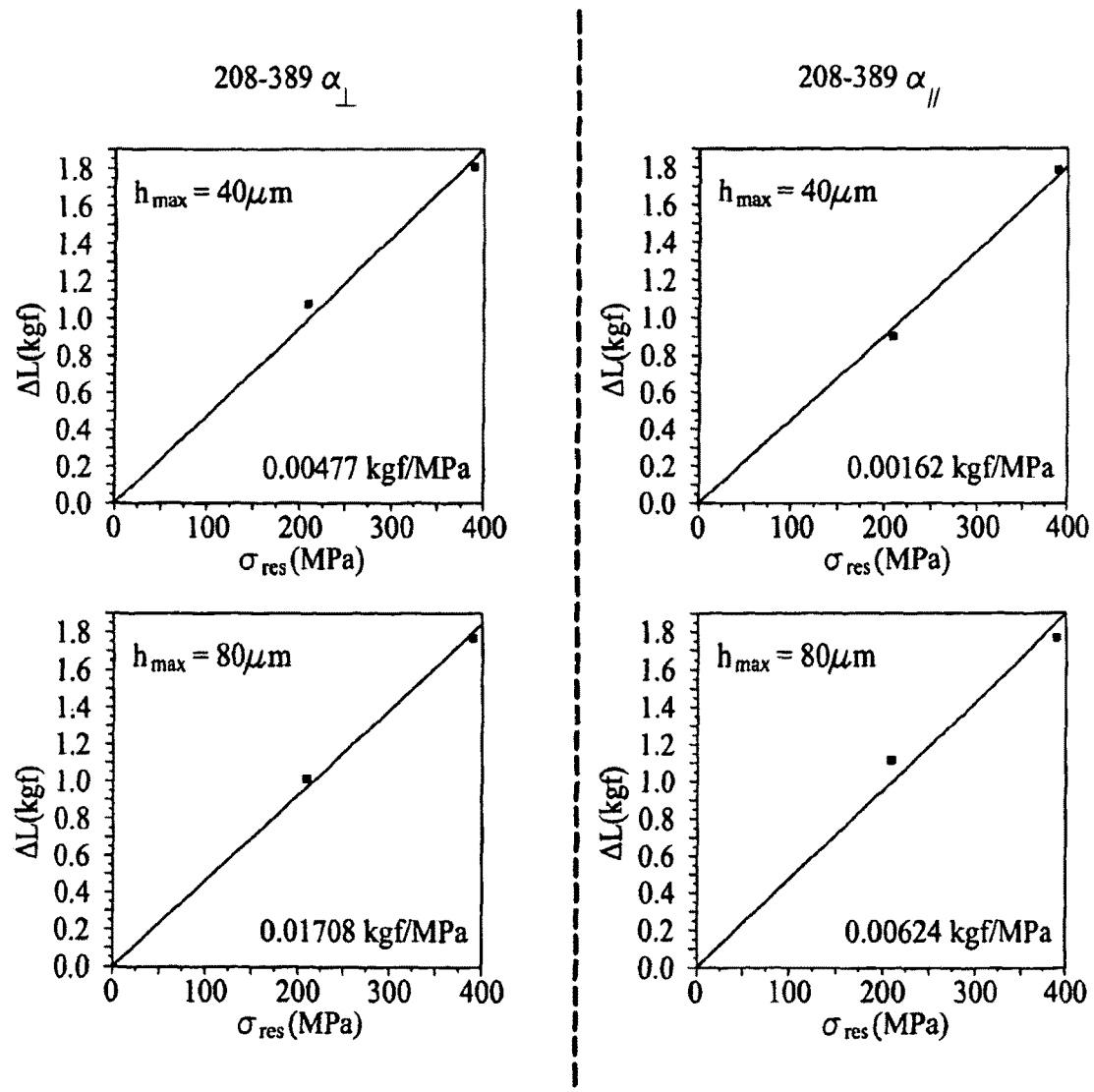

[Figure 24]
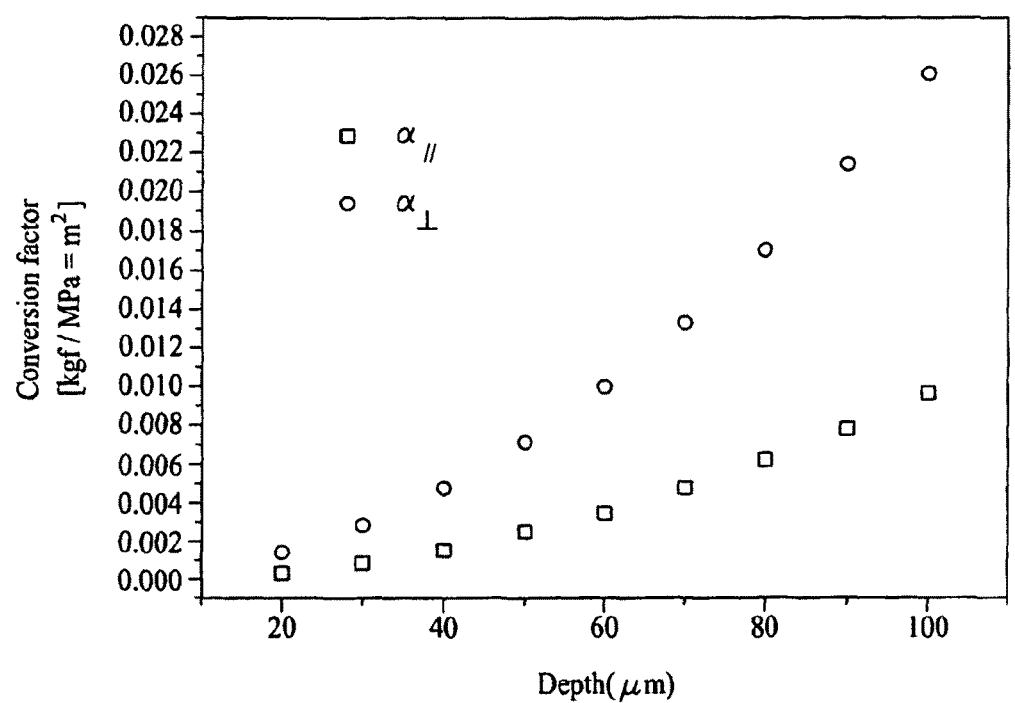

[Figure 25]
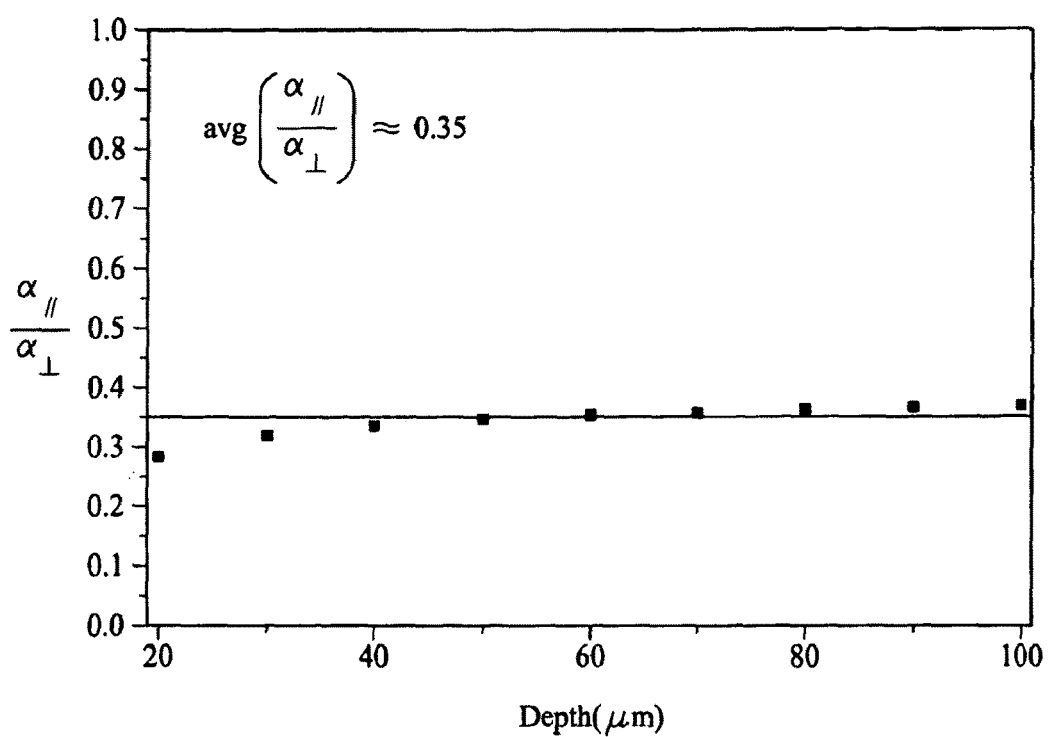

[Figure 26]
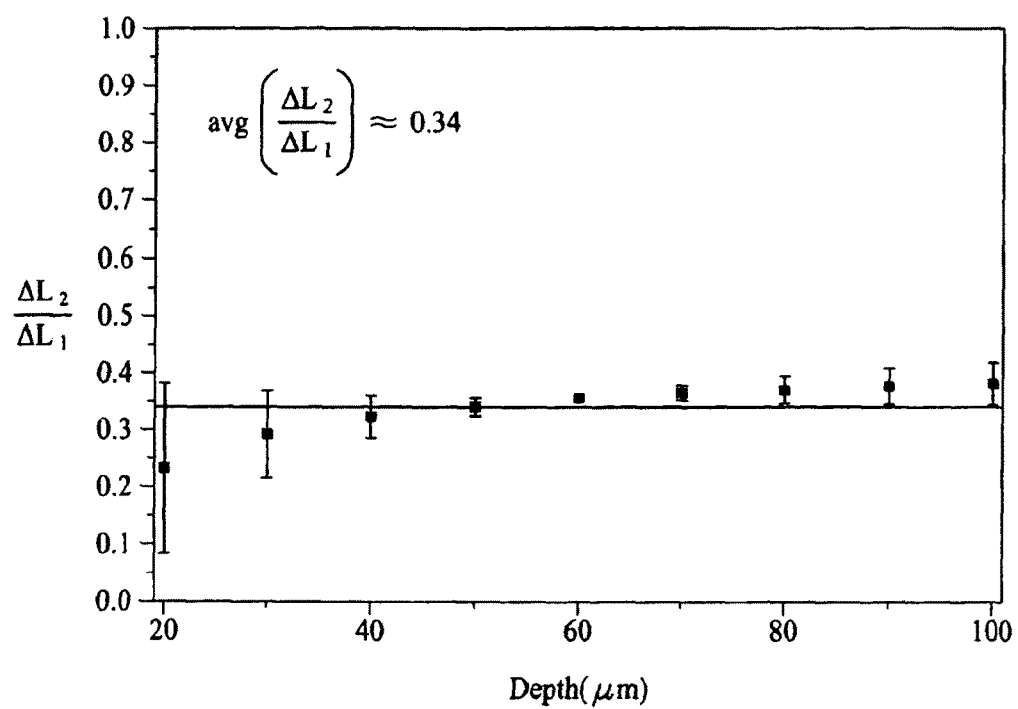

[Figure 27]
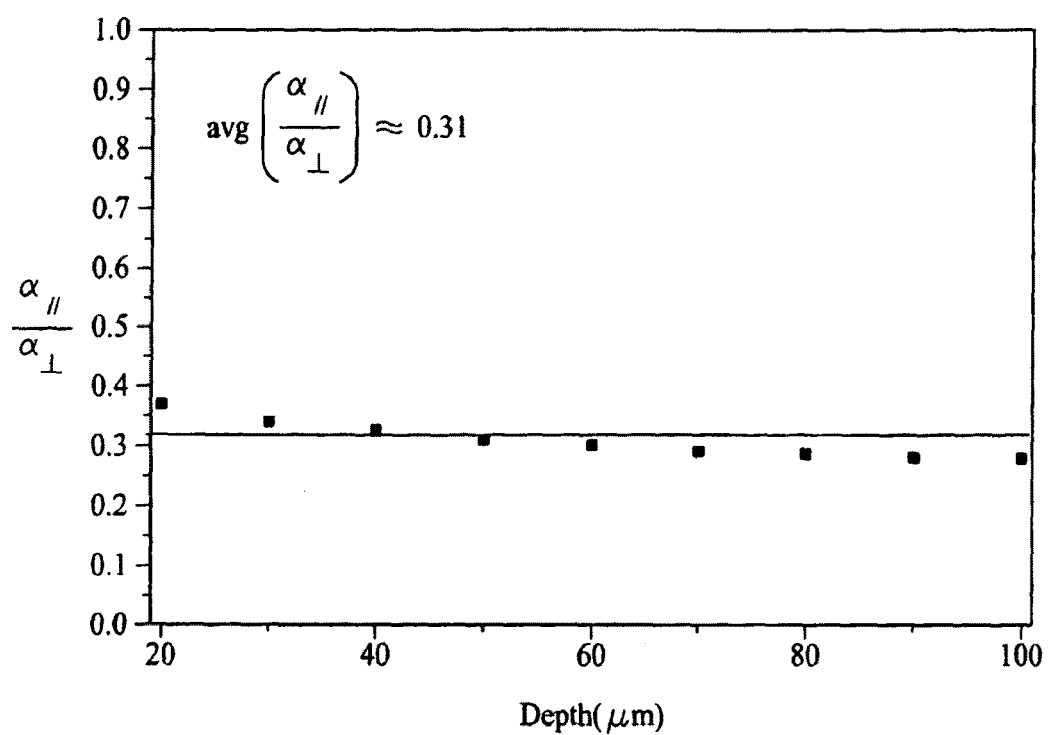

[Figure 28]
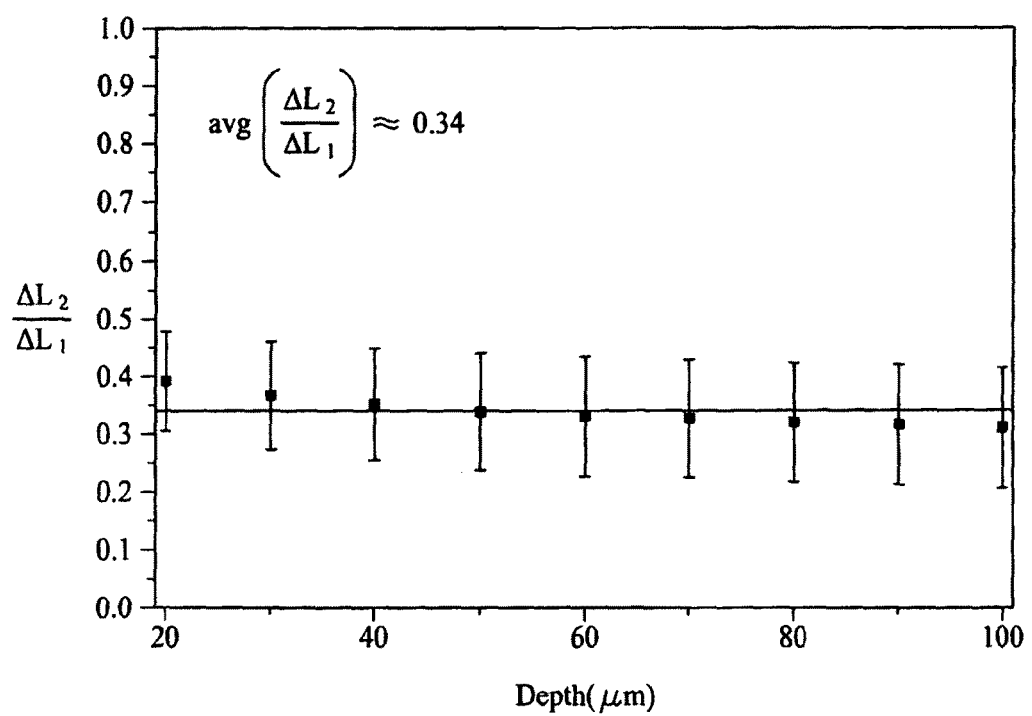

[Figure 29]
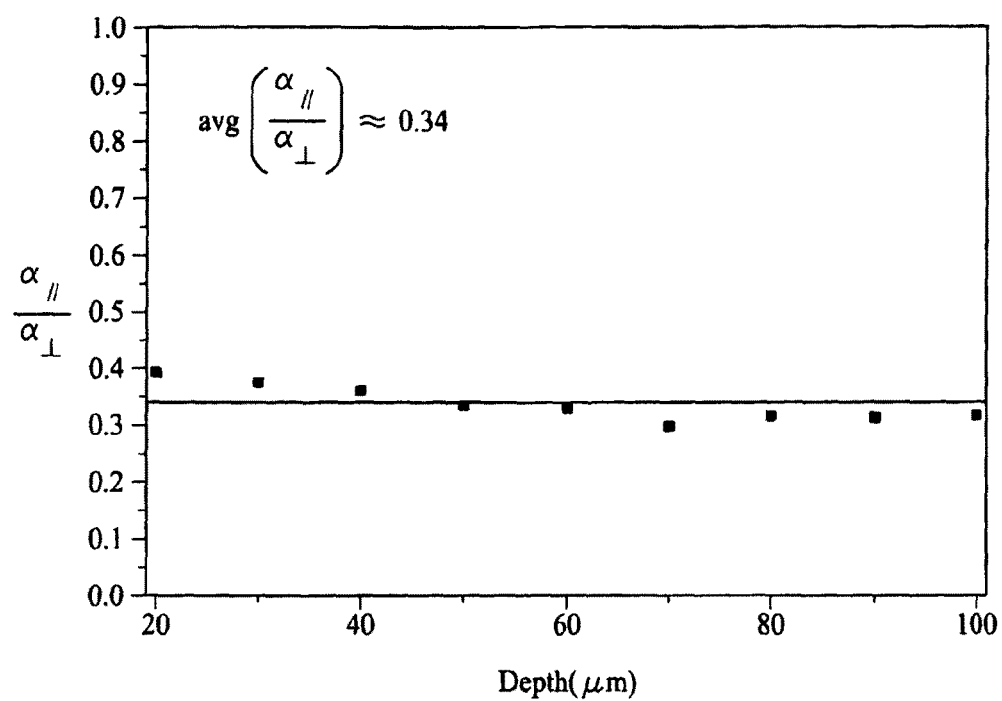

[Figure 30]
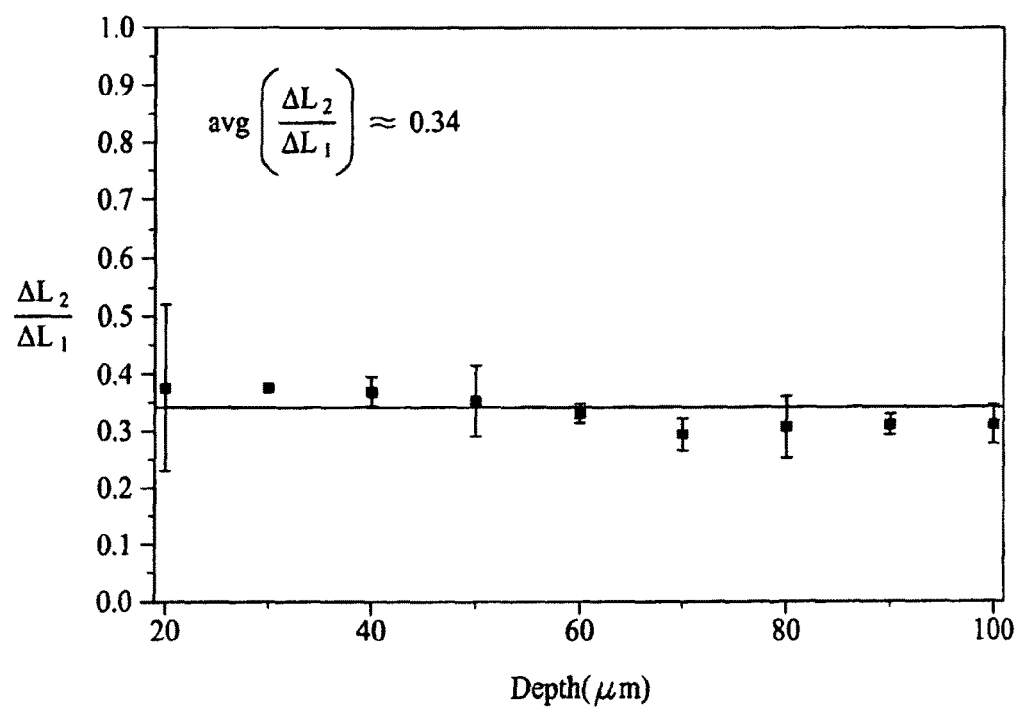

[Figure 31]
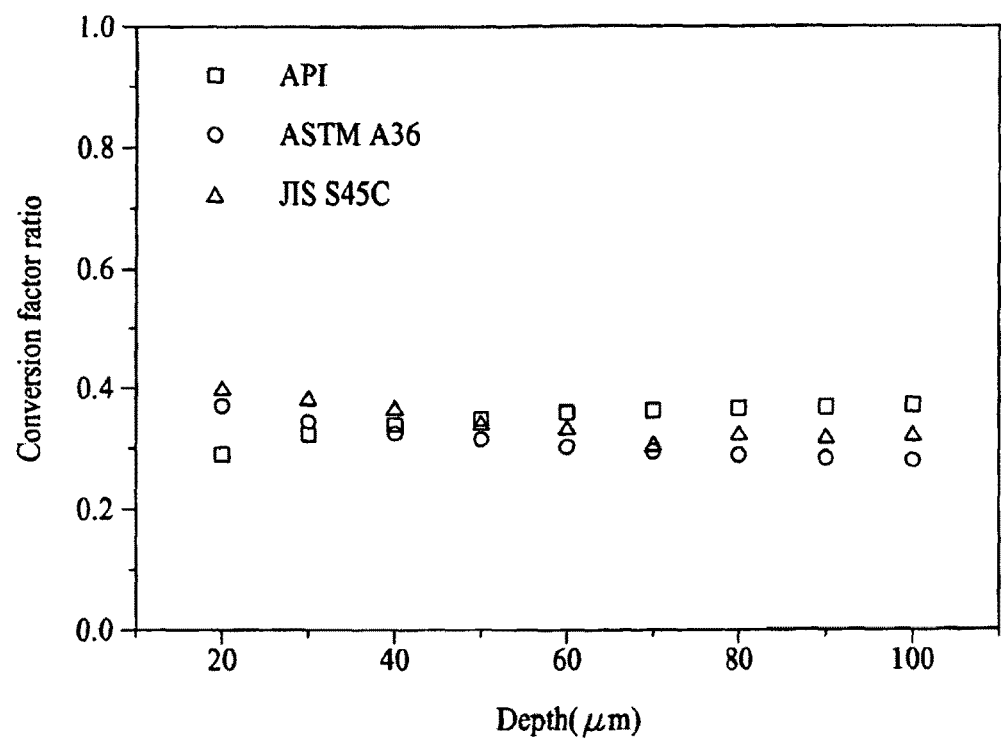

[Figure 32]
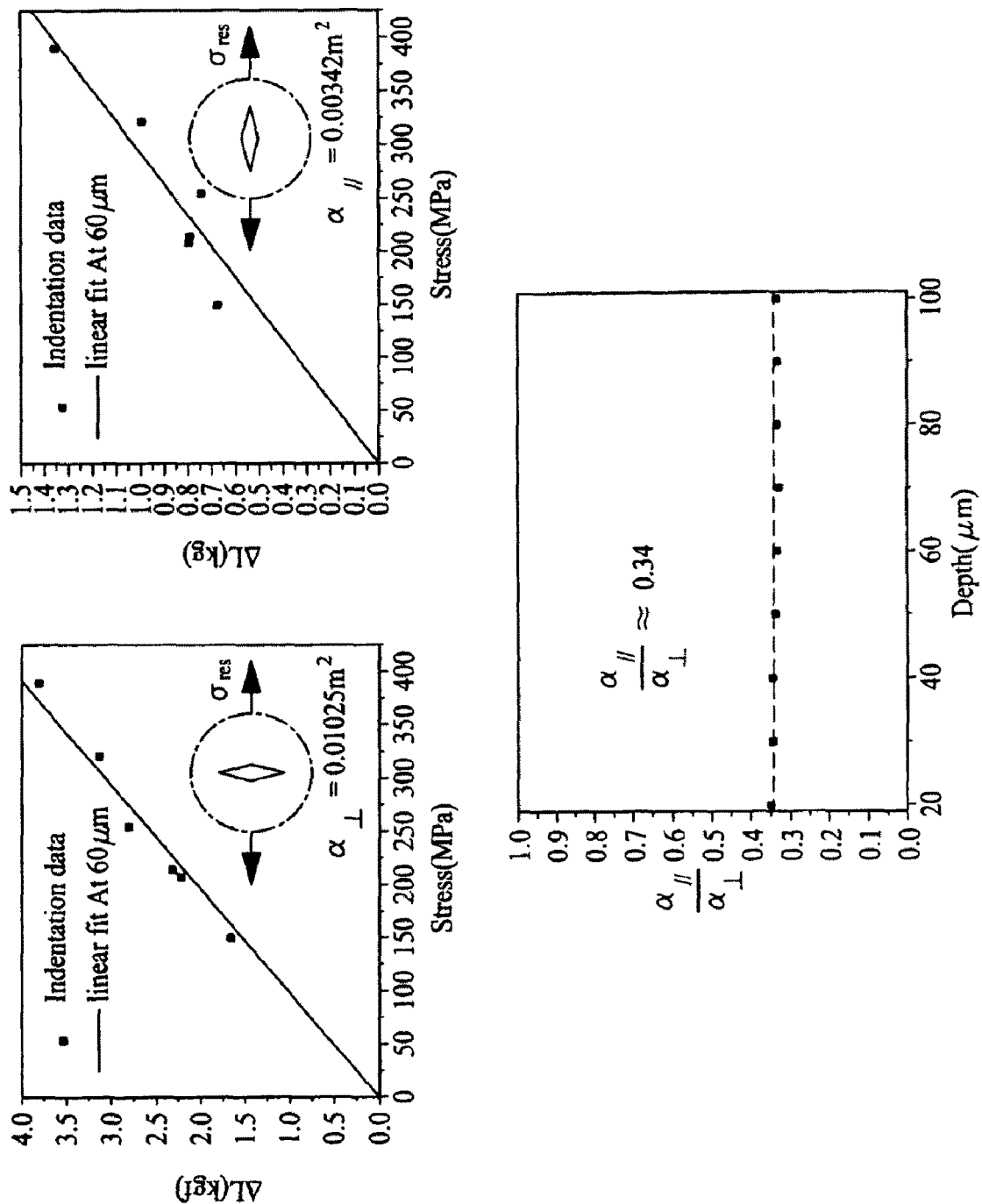

[Figure 33]
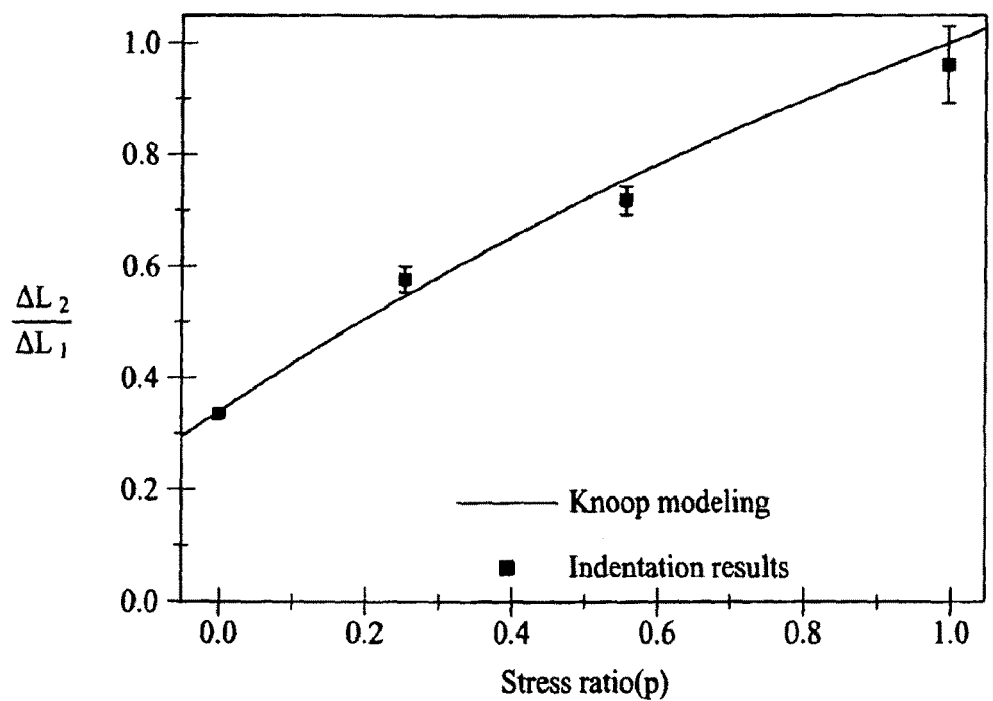

[Figure 34]
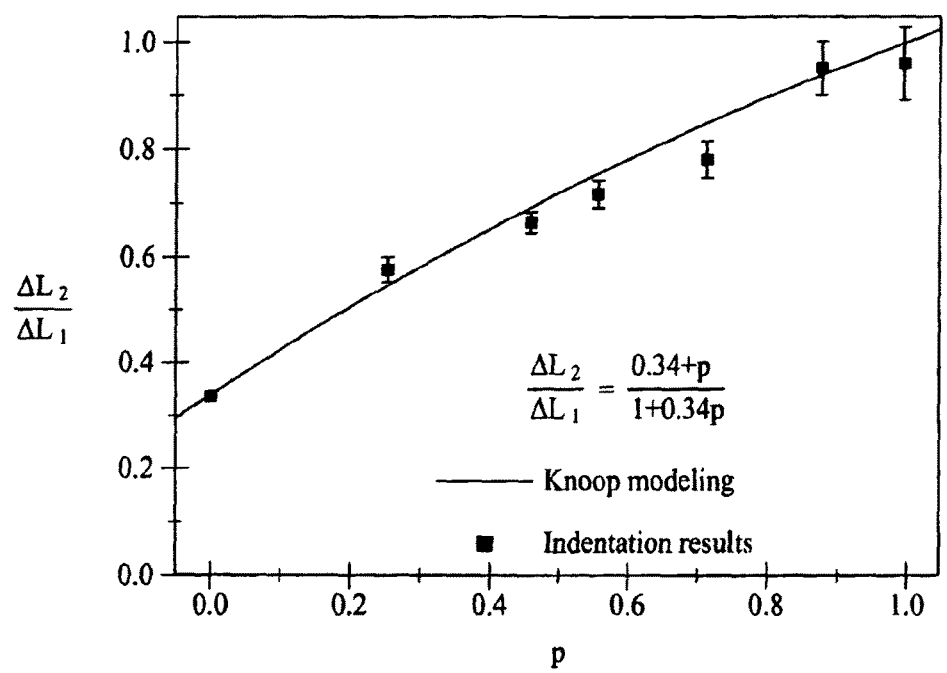

[Figure 35]
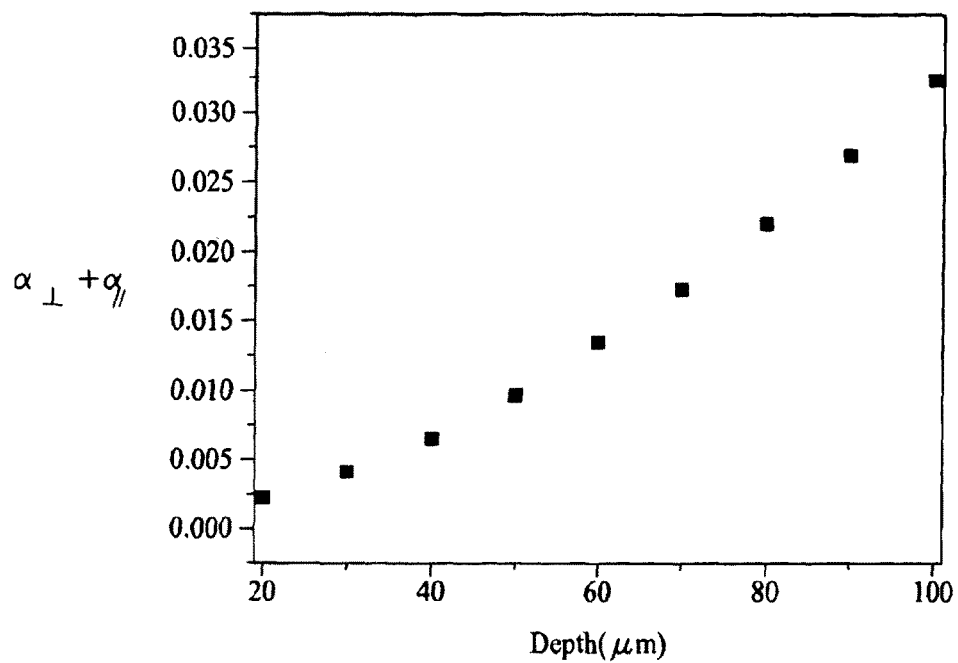

[Figure 36]
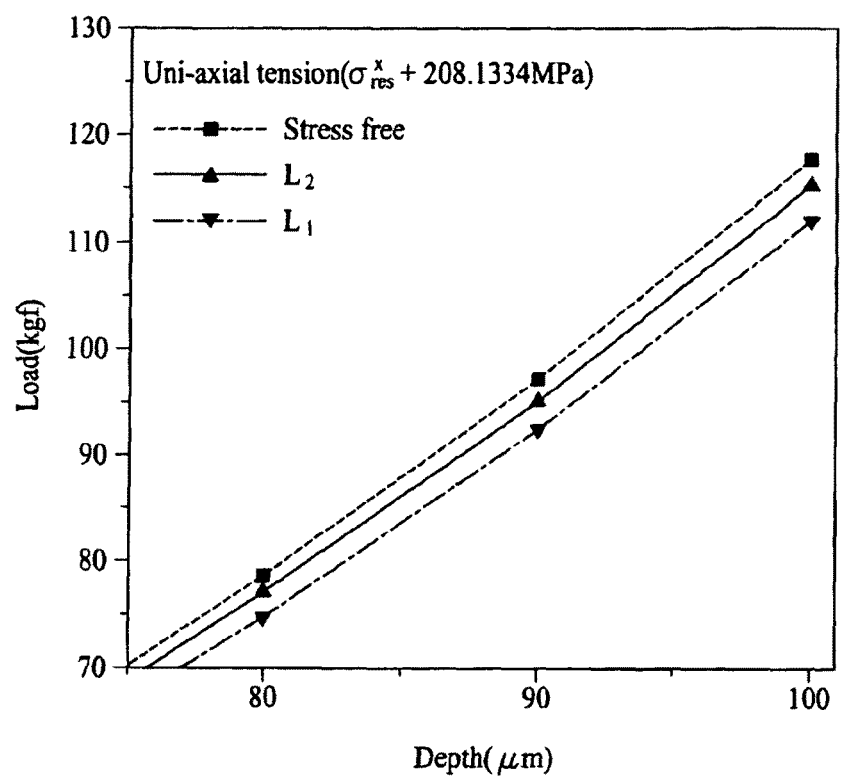

[Figure 37]
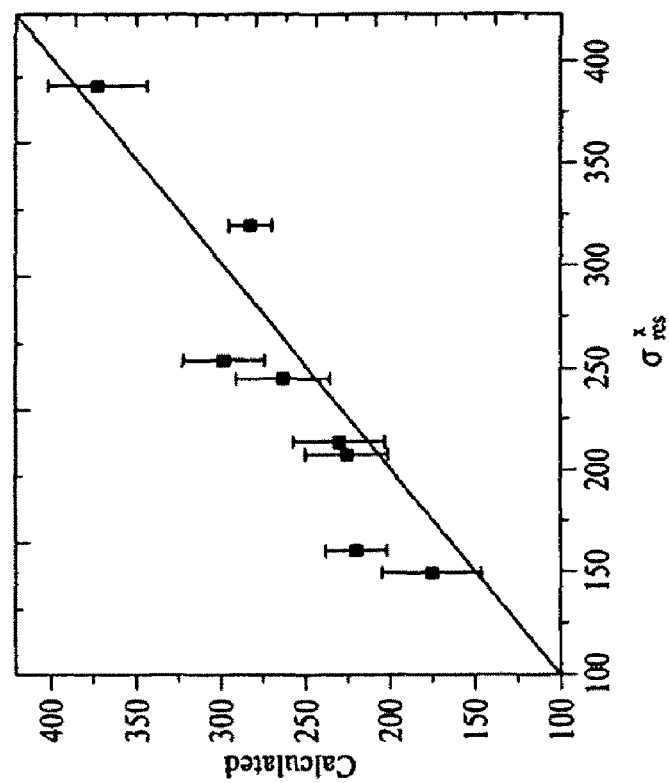
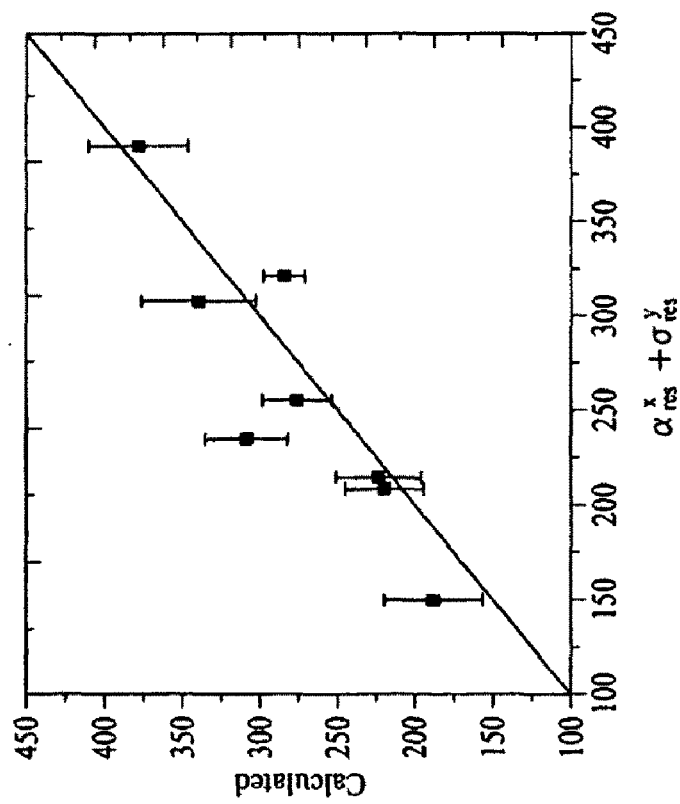

[Figure 38]
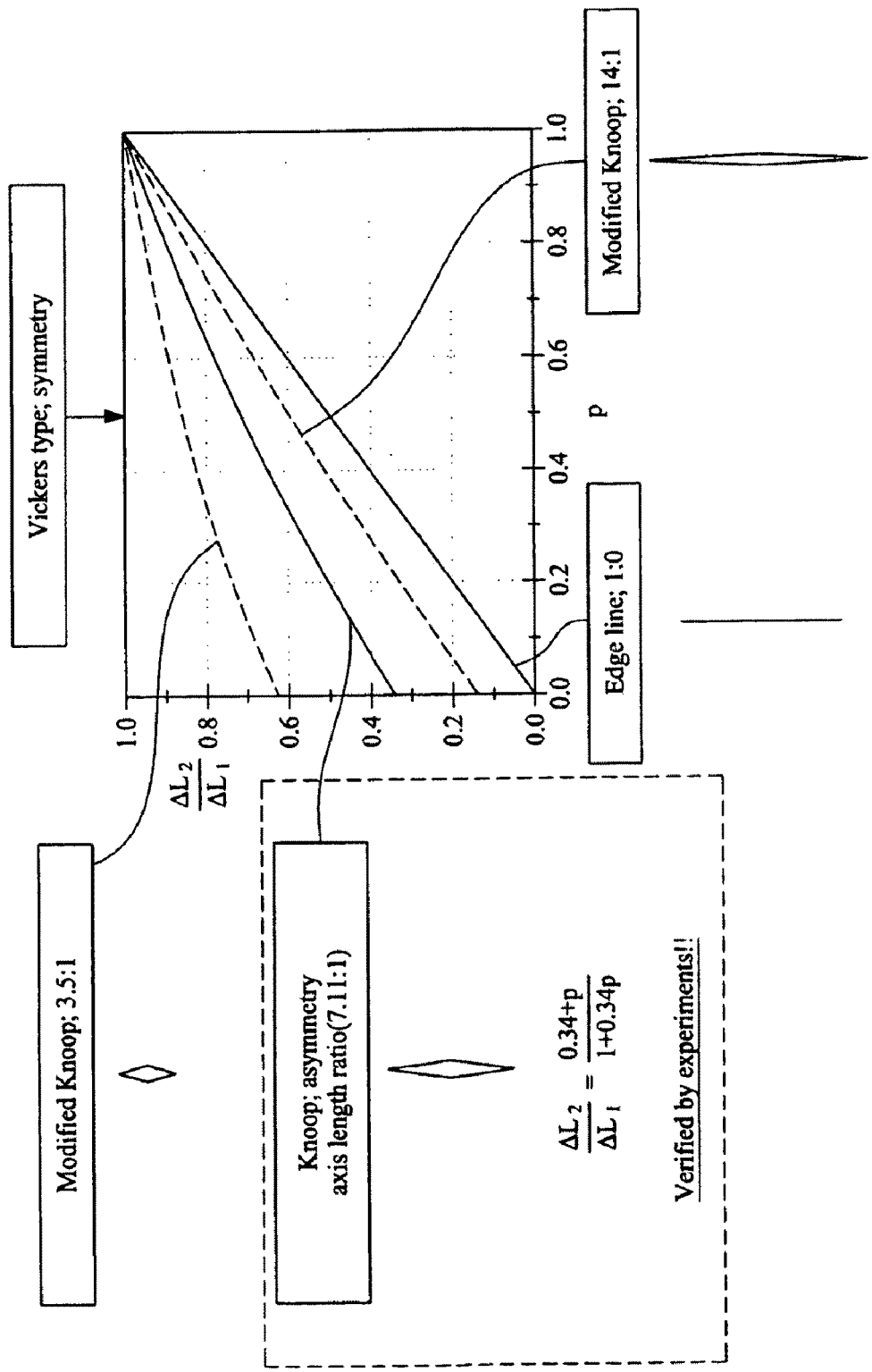

[Figure 39]
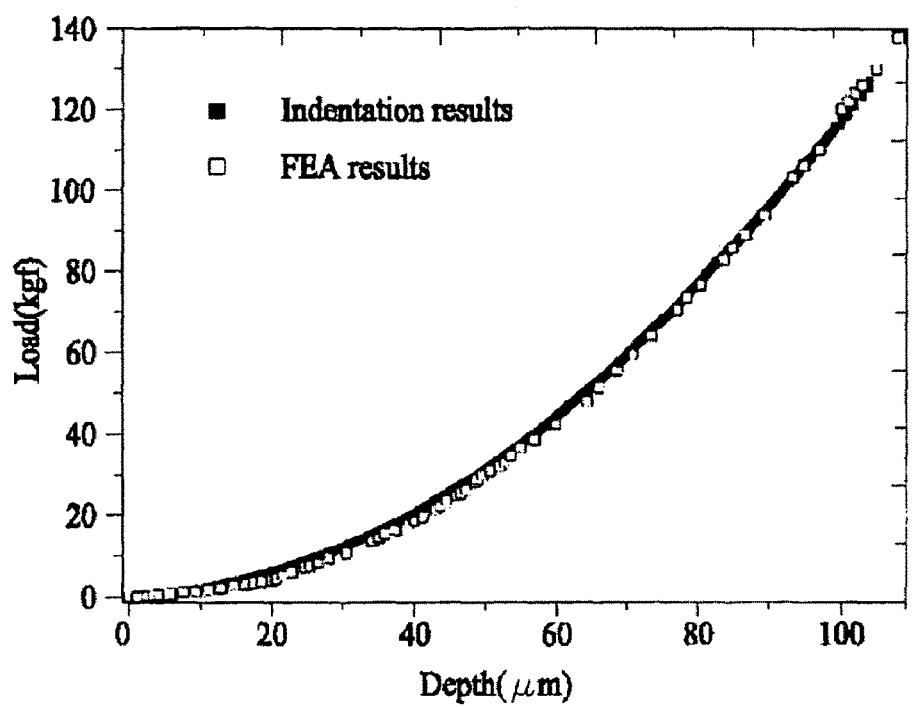

[Figure 40]
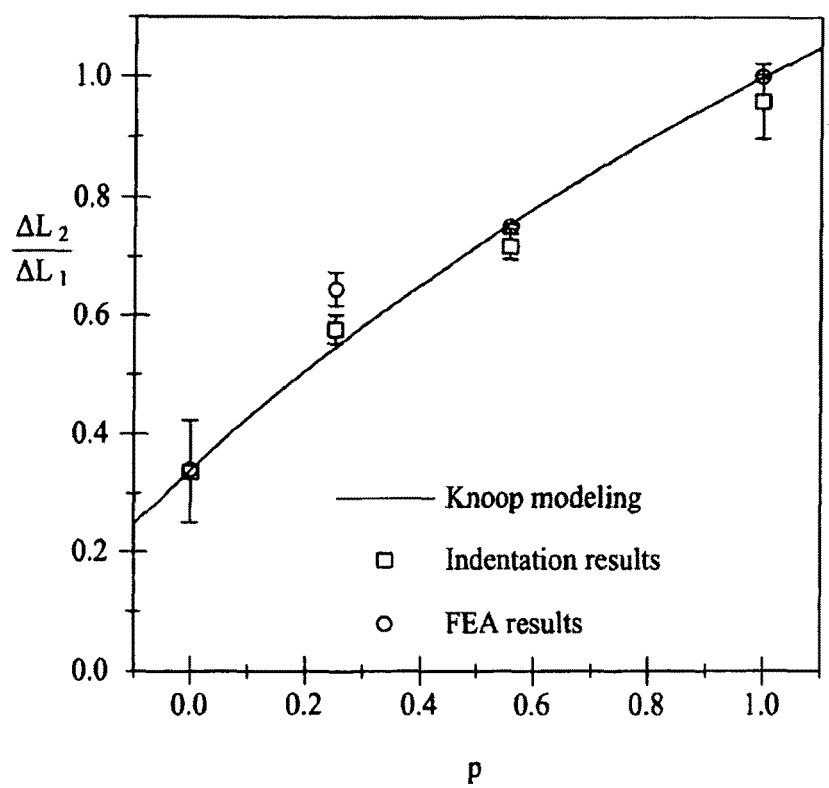

[Figure 41]
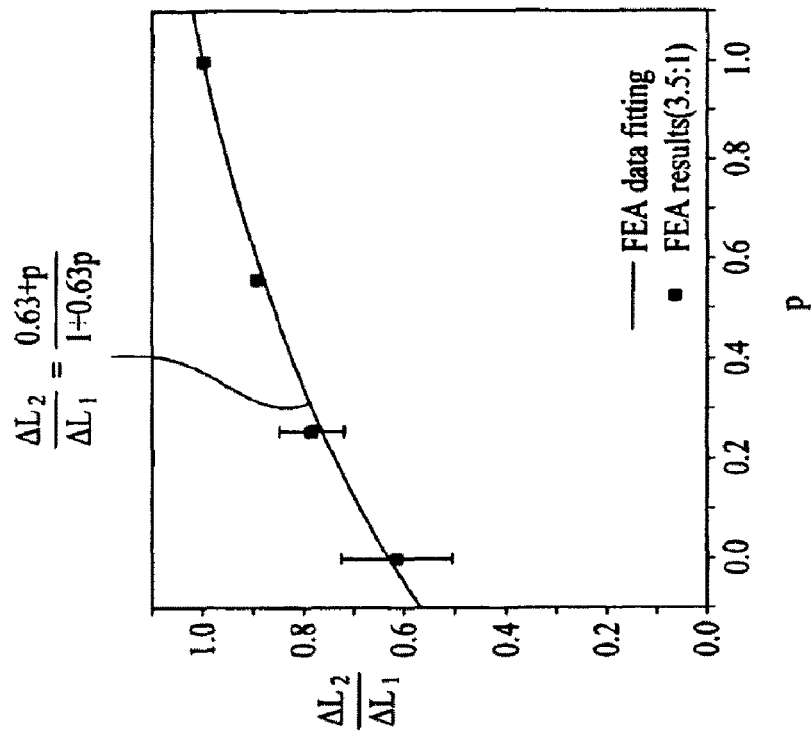
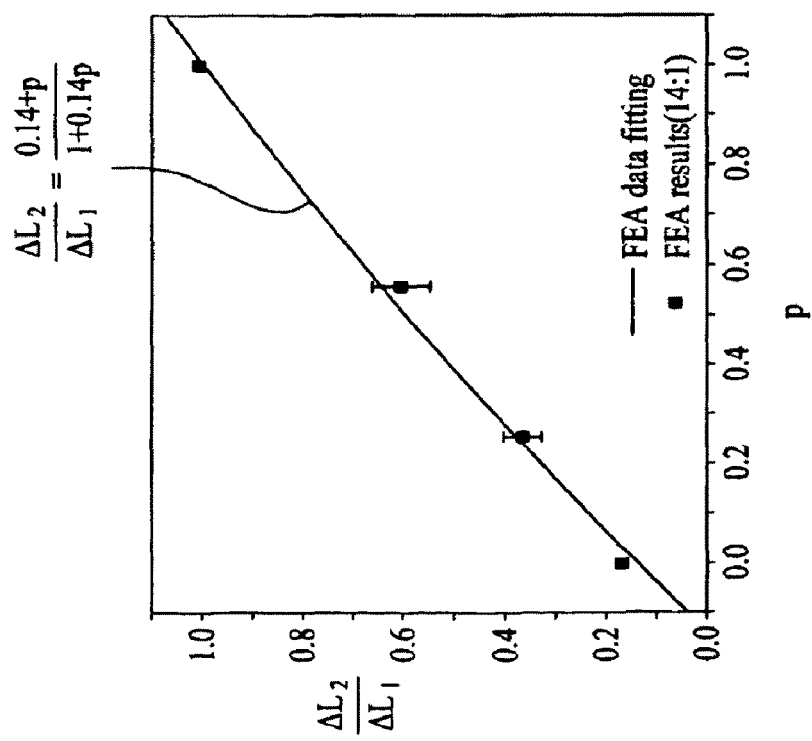

ESTIMATION OF NON-EQUIBIAXIAL STRESS USING INSTRUMENTED INDENTATION TECHNIQUE

TECHNICAL FIELD

The present invention relates to an instrumented indentation method to non-destructively estimate the mechanical material property. Also, the present invention relates to an estimation of non-equibiaxial residual stress to be applied to an in-field structure and a weldment.

BACKGROUND ART

Conventional methods for measuring residual stress are classified into destructive and non-destructive types dependent on the destruction of estimated materials. There needs to introduce non-destructive type for estimating residual stress for structures or facilities under construction or in service because it's impossible for them to apply to destructive type.

Conventional methods for measuring residual stress are described that repeatedly measure variation of an indention depth according to continuous indentation of the indenter on the surface of samples and calculate the residual stress based on the measured results such as the indentation load and depth.

For example, there are described "Apparatus for determining residual stress, method for determining residual stress data using it, residual stress determining method using it and recording medium thereof" in Korean patent No. 0416723 and "Estimating method of residual stress using continuous indentation" in Korean patent No. 0517857.

DISCLOSURE

Technical Problem

One object of the present invention is to non-destructively estimate non-equibiaxial residual stress among the mechanical material properties using a non-equibiaxial indenter.

Technical Solution

In one aspect, The present invention provides a method for evaluating an asymmetric residual stress for a material by the indentation test. The method comprises: applying the residual stresses with an uniaxial and an symmetrical biaxial tensions on the material and then performing an instrumented indentation test indenting an asymmetric indenter on the material; and comparing a slope of indentation load-depth curve when the long diagonal direction of the asymmetric indenter is perpendicular to the direction of the largest residual stress with that in stress-free state, and then a slope of indentation load-depth curve when the long diagonal direction of the asymmetric indenter is parallel to the direction of the largest residual stress with that in stress-free state, so as to evaluate the asymmetric residual stress for the material.

The asymmetric indenter may have geometry of 7.11:1 for long and short diagonal lengths.

The method may further comprise: determining the ratio of the conversion factor ($\alpha_\perp$, $\alpha_{//}$) which associates the residual stress with the induced indentation load difference from the residual stress according to the uniaxial residual stress and the longer diagonal direction of the asymmetric indenter; and using the conversion factor ratio and the ratio of the induced indentation load differences ($\Delta L_1$ and $\Delta L_2$) when the long diagonal direction of the asymmetric indenter in the biaxial residual stress state is perpendicular or parallel to the direction of the largest residual stress, then to determine the stress directionality (p).

The conversion factor ratio may be 0.34.

The stress directionality (p) may be determined by the formula below with the conversion factor ratio and the indentation load difference ratio.

$$\frac{\Delta L_2}{\Delta L_1} = \frac{\frac{\alpha_{//}}{\alpha_\perp} + \frac{\sigma_{res}^y}{\sigma_{res}^x}}{1 + \frac{\alpha_{//}}{\alpha_\perp}\frac{\sigma_{res}^y}{\sigma_{res}^x}} = \frac{\frac{\alpha_{//}}{\alpha_\perp} + p}{1 + \frac{\alpha_{//}}{\alpha_\perp}p}$$

The method may further comprise: solving the simultaneous equations in the formula below which contains the conversion factor, and the ratio and the sum of the residual stress, and determining the residual stress of both of the longer and shorter diagonals.

$$p = \frac{\sigma_{res}^y}{\sigma_{res}^x} = \frac{\frac{\Delta L_2}{\Delta L_1} - 0.34}{1 - 0.34\frac{\Delta L_2}{\Delta L_1}}$$

$$\sigma_{res}^x + \sigma_{res}^y = \frac{\Delta L_1 + \Delta L_2}{\alpha_\perp + \alpha_{//}}$$

The method may further comprise: confirming a relationship between the geometry of the asymmetric indenter and the conversion factor ratio through the Finite Element Analysis.

In other aspect, the present invention provides a computer-readable medium comprising a program for execution on a computing device, wherein the program comprising; steps of the Method for evaluating an asymmetric residual stress for a material by the indentation test.

In another aspect, the present invention provides an instrumented indentation apparatus for applying an instrumented indentation test by executing a computer-readable medium comprising a program for execution on a computing device, wherein the program comprising; steps of the method for evaluating an asymmetric residual stress for a material by the indentation test.

Advantageous Effects

The present invention is advantageous in that non-equibiaxial residual stress among the mechanical material properties is non-destructively estimated.

DESCRIPTION OF DRAWINGS

FIG. 1 is a perspective view of indenter applied to one embodiment of the present invention.

FIGS. 2, 3, 4 and 5 show the expression of equations and the procedure for an instrumented indentation test using an asymmetric indenter according to one embodiment of the present invention.

FIG. 6 shows that what the residual stress of each different axis affects the indentation load can be expressed in the form of the summation.

FIG. 7 shows experimentally that the sum of the indentation load from the uniaxially applied residual stresses is substantially equal to the indentation load difference from the biaxially applied residual stresses inside 5% range except for the initial indenting range.

FIG. 8 shows that the indentation hardness was inclined to be either the smallest or the largest when the direction of the residual stress, and the long diagonal direction of the Knoop indenter is either parallel or perpendicular to each other.

FIG. 9 shows that the stress-induced pile-up shift ratio on or near the biaxially measured impression of indentation is proportional to the residual stress ratio.

FIG. 10 shows the procedures to solve the equations for the instrumented indentation test according to one embodiment of the present invention.

FIGS. 11 and 12 show the new jig apparatus which is invented for applying the asymmetric biaxial surfacial residual stress ($\sigma^x_{res} \neq \sigma^y_{res} \neq 0$, $\sigma^z_{res}=0$) to a cruciform specimen, or a beam or rectangular specimen.

FIG. 13 shows the previous asymmetric Knoop indenter with 7.11:1.

FIG. 14 is the photograph of the Knoop indenter.

FIG. 15 shows the measured values of the Knoop indenter of FIG. 14.

FIG. 16 is the photograph of the instrumented indentation equipment applied to one embodiment of the present invention.

FIG. 17 shows that when the spherical indenter indents an API X-65 material at the maximum 150 μm, and the average size of grains is 10 μm, there are about tens thousand grains within plastic zone and millions grains within elastic zone.

FIG. 18 shows that the grind condition of the surface is determined and the indentation speed is determined 0.1 mm/min.

FIG. 19 is a mimetic diagram of the applied experiment for determining the conversion factor.

FIGS. 20 to 22 show the results when they are overlapped with the curve in stress-free state.

FIG. 23 includes the graphs to linearly connect the load differences with the starting point of coordinate when the uniaxial residual stresses of 208, 389 MPa are applied.

FIG. 24 draws the conversion factors $\alpha_\perp$, $\alpha_{//}$ according to the indentation depth.

FIGS. 25 and 26 show the conversion factor ratios for API X-65.

FIGS. 27 and 28 show the conversion factor ratios for ASTM A35.

FIGS. 29 and 30 show the conversion factor ratios for JIS S45C respectively.

FIG. 31 comparatively show the conversion factor ratios for the above three steels at each depth at the same time.

FIG. 32 shows that it is found that the indentation load difference is generated relative to the amount of the residual stress regardless of the material.

FIG. 33 shows that the indentation load difference from the instrumented indentation test for API X-65 is compared with the actual residual stress ratio p when various kinds of residual stresses are applied.

FIG. 34 shows the ratio of the indentation load difference from the instrumented indentation test to the actual residual stress after the residual stress with the biaxial tension is applied to the three kinds of steels in this specification.

FIG. 35 is the graph to show the sum of the conversion factors, $\alpha_\perp$, $\alpha_{//}$ according to indentation depth.

FIG. 36 shows the result of the Knoop indentation test for the API X-65 cruciform specimen to which the residual stress with uni-axial tension of 208 MPa is applied.

FIG. 37 shows the calculated residual stresses from the above procedure when the simultaneous equations in equation 14 and 15 are solved.

FIG. 38 shows that as the asymmetry is larger, so it may be reflected of its effect on a large scale.

FIG. 39 shows that the experimental result when the Knoop indenter is indented on API X-65 of stress-free state is compared with that obtained by using the FEA.

FIG. 40 show the result from the computer mimitation after the biaxial residual stress equal to the actual experimental value is applied.

FIG. 41 shows the result from FEA in residual stress states with various biaxial tensions(p=0, 0.25, 0.5, 1) when the ratios of long and short diagonal lengths in the asymmetric indenter are a 3.5:1 and 14.1.

MODE FOR INVENTION

Hereinafter, an exemplary embodiment of the present invention will be described with reference to the accompanying drawings.

1. Introduction

Residual stress is defined as stress that remains inside the materials after external forces, heat gradient or constraint conditions has been removed. That occurs on heat treatment, welding, casting, cutting, drawing, rolling, extruding, shot peening, coating and the like during all kinds of manufacture or processing. In case of welding, there exists residual stress substantially equal to yield strength. In case of complex materials or thin film, there is accumulated residual stress because of mutual restraint on an interface.

Residual stress affects the intensity and mechanical property of materials. Residual stress affects progress or deterioration of a fatigue, destruction, corrosion and the like. Therefore, it is very important to perform the accurate analysis for residual stress from structures or facilities to ultrastructures such as electronic products.

Conventional methods for measuring residual stress are mainly classified into destructive and non-destructive types dependent on the destruction of estimated materials, as described above. It is impossible for conventional methods to be applied to materials under the construction because of destructing materials or the restraint of samples and the like. The instrumented indentation method, which is easy to perform on the construction and can characterize materials on local scale, has recently attracted significant research interest because it is non-destructive and easy to prepare the sample.

It is possible for the instrumented indentation method to be applied to all areas from nano to macro scales. The mechanical properties such as residual stress, hardness and modulus of elasticity can determined by continuously measuring load and depth values and analyzing the indentation load-depth curves.

There are numerous methods to evaluate residual stress. Among these, the instrumented indentation method can evaluate residual stress by analyzing both the indentation load difference between stress-free state without residual stress and stress state with residual stress and the difference of contact areas thereon.

However, this method using a symmetric indenter is limited to an equibiaxial residual stress state because of measuring only the average residual stress. It has been known that the actual residual stresses on most of the existed materials except for the thin film are the non-equibiaxial residual stresses.

This inventor has determined the directionality of residual stress using an asymmetric or non-equi indenter such as Knoop indenter. Generally, Knoop indentation method has been applied to an asymmetry or asymmetry research on materials. The Knoop indenter is asymmetric indenter with elongated four-sided pyramidal geometry of which has a 7.11:1 for long and short diagonal lengths, referring to FIG. 1. It is proved mathematically and found experimentally that the change on the load-depth curve is dependent on the penetration direction of the Knoop long diagonal by using the Knoop indenter. Only the Knoop indenter is used to determine residual stress for each axis.

The previous study, Y. H. Lee and D. Kwon (Y. H. Lee and D. Kwon: Acta Mater., Vol. 52 (2004) p. 1555) found that the slope of indentation load-depth curve is changed dependent on the existence of residual stress when indented by an equi-indenter. When indented to keep the maximum indentation depth constant, tensile residual stress leads to the decrease of contact area because of sink-in. Otherwise, compressive residual stress leads to the increase of contact area and indentation load because of pile-up. It is found that the load differences are proportional to the increase of residual stress. As described above, using a symmetric equi-indenter is limited to measuring only the average residual stress without determining asymmetry coefficient of residual stress.

Therefore, the specification develops a model to determine asymmetry coefficient of residual stress by using Knoop indenter in FIG. 1 as non-equi indenter. The Knoop indenter is introduced from F. Knoop, C. G et al. (F. Knoop, C. G. Peters and W. B. Emerson: J. Nat. Bur. Stand., Vol. 23 (1939) p. 39).

Vickers indenter as an equi indenter is limited to measuring only the average residual stress because of symmetrical geometry of Vickers indenter. It is difficult to perform quantitative analysis of the residual stress without knowing the asymmetry coefficient p of residual stress, as expressed in equation 1. However, it is possible to measure only the average residual stress. The relationship between the indenation load differences and the average residual stress is expressed in equation 2.

$$\sigma_{res}^x = \frac{3}{1+p} \frac{L_0 - L_S}{A_S},$$ [Math FIG. 1]

$$\sigma_{res}^y = p\sigma_{res}^x$$

$$\sigma_{res} = \sigma_{res}^x + \sigma_{res}^y$$ [Math FIG. 2]

$$= \frac{3(1+p)}{1+p} \frac{L_0 - L_S}{A_S}$$

$$= 3\frac{L_0 - L_S}{A_S}$$

Wherein $\sigma_{res}$ is the penetration direction of the Knoop long diagonal, p is the asymmetry coefficient, and $L_0$-$L_S$ is the load difference. A is calculated by the Oliver Pharr method.

It is difficult to predict or measure the contact area when the residual stress is applied because of the transformation of complicated indentation morphology. It is possible to determine the contact area from $A_0L_S/L_0$ based on the previous study (T. Y. Tsui, W. C. Oliver and G. M. Pharr: J. Mater. Res., Vol. 11 (1996) p. 752) that the indentation hardness is constant. Wherein $A_0$ and $L_0$ are the contact area and the indentation load in stress-free state, respectively.

It is possible to easily calculate the contact area in stress-free state by Oliver-Pharr method (W. C. Oliver and G. M. Pharr: J. Mater. Res., Vol. 7 (1992) p. 1564). The indentation load difference $L_0$-$L_S$ can be derived as the difference of loads in stress-free state and stressed state at the same indentation depth. If there is newly introduced the conversion factor α which changes the indentation load into the residual stress, The equation 2 is expressed as equation 3.

$$\sigma_{res} = \frac{3}{A_0} \frac{L_0(L_0 - L_S)}{L_S}$$ [Math FIG. 3]

$$= \alpha \frac{L_0(L_0 - L_S)}{L_S}$$

The equation 3 can be expressed as equation 4.

$$L_S = \frac{L_0^2}{\alpha\sigma_{res} + L_0}$$ [Math FIG. 4]

When $L_S$ in equation 4 is added to that in equation 3, the relationship between the indentation load difference ΔL and the sum of residual stress is obtained.

$$\Delta L = L_0 - L_S$$ [Math FIG. 5]

$$= \frac{\alpha\sigma_{res}L_0}{\alpha\sigma_{res} + L_0}$$

$$= \frac{\alpha\sigma_{res}}{\alpha\sigma_{res}/L_0 + 1}$$

$$= \alpha\sigma_{res}$$

$$= \alpha\sigma_{res}^x + \sigma_{res}^y$$

Because α $\sigma_{res}/L_0$ is relatively less than 1, there can be expressed as equation 5. The specification proves theoretically that the residual stress experimentally obtained from the previous study is propositional to the load difference induced from the residual stress.

2. Modeling 2.1. Determination of Directionality of Residual Stress

The Knoop indenter is the asymmetric indenter with elongated four-sided pyramidal geometry of which has a 7.11:1 for long and short diagonal lengths, as shown in FIG. 1. The Knoop indenter yields a indentation load-depth curve changed according to the indenting direction because the asymmetric residual stress functions biaxially, as shown in FIG. 2. Because the tensile residual stress is applied biaxially, the slope of the indentation load-depth curve is lower than that in stress-free state regardless of the indenting direction. When there is applied the tensile residual stress having the longer x-axis diagonal length than y-axis diagonal length, the slope of that where the long diagonal of Knoop indenter is perpendicular to the x-axis is relatively the lowest value, while the slope of that where the long diagonal of Knoop indenter is parallel to the x-axis is relatively the highest value.

It is confirmed through this experiment that the load difference ratio can be expressed as a function of residual stress ratio p. $\Delta L_1$ can be defined as the difference of loads between the intended state where the long diagonal of Knoop indenter is perpendicular to the x-axis and stress-free state at the same indentation depth. $\Delta L_2$ can be defined as the difference of loads between the intended state where the long diagonal of Knoop indenter is parallel to the x-axis and stress-free state at the same indentation depth.

As to the above equation, the indentation load difference induced from the residual stress at Vickers indentation is proportional to the residual stress of each axis. There is obtained the indentation load-depth curve in the form of the summation, as shown in FIG. 3.

It can be proposed that the applied residual stress is proportional to the indentation load difference for the Knoop indenter with elongated four-sided pyramidal geometry, similar to the Vickers indenter. However, It can be proposed that the relationships between the residual stresses of the long diagonal and the short diagonal, and the indentation load for the asymmetric Knoop indenter are expressed as the equation 6, to introduce the conversion factors, $\alpha_\perp$, $\alpha_{//}$, according to the residual stress and the indenting direction, as shown in FIGS. 4 and 5.

$$\Delta L_1 = \alpha_\perp \sigma_{res}^x + \alpha_{//} \sigma_{res}^y$$

$$\Delta L_2 = \alpha_{//} \sigma_{res}^x + \alpha_\perp \sigma_{res}^y \quad \text{[Math Figure 6]}$$

The experiment shown in FIG. 6 is performed to prove the assumption that the effect of the residual stress of each different on the indentation load can be expressed in the form of the summation. The sum of the indentaion load difference in that the long diagonal of the indenter is perpendicular and parallel to the direction of the uniaxially applied residual stress of 200 MPa is compared with the load difference of the biaxially applied residual stress of 200 MPa.

The indentaion load-depth curve when the long diagonal of the indenter is perpendicular to the direction of the indented residual stress, can be defined as $L_1$, while the indentaion load-depth curve when the long diagonal of the indenter is parallel to the direction of the indented residual stress, can be defined as $L_2$.

If the sum of the indentation load from the uniaxially applied residual stresses is substantially equal to the indentation load difference from the biaxially applied residual stresses, it may be confirmed that the relationship between the indentation load difference and the residual stress from equation 6 is valid or well-directed. FIG. 7 shows experimentally that the sum of the indentation load from the uniaxially applied residual stresses is substantially equal to the indentation load difference from the biaxially applied residual stresses inside 5% range except for the initial indenting range. The assumption is proved through this experiment that the effect of the residual stress of each different on the indentation load can be expressed in the form of the summation.

The previous study to relate the Knoop indenter to the residual stress by Oppel (G. U. Oppel: Experimental Mech., Vol. 4 (1964) p. 135) found that the indentation hardness was inclined to be either the smallest or the largest when the direction of the residual stress is either parallel or perpendicular to the long diagonal direction of the Knoop indenter, as shown in FIG. 8. The indentation hardnesses from the 45°, 135° rotations are the values between $\Delta H_1$ and $\Delta H_2$, and equal to each other. Because $\Delta H_1 + \Delta H_2 = \Delta_{45}° + \Delta H_{135}°$, it is found that shear strain doesn't affect the indentation hardness change while normal strain affects that.

It is found that the perpendicularly applied residual stress affects the indentation hardness change. As described in the previous study, $\Delta L_1$ and $\Delta L_2$ can be derived as the sum of the indentation load differences from the residual stress by each axis.

The ratio of $\Delta L_1$ and $\Delta L_2$ can be expressed as the residual stress ratio p which defines the directionality of the residual stress.

$$\frac{\Delta L_2}{\Delta L_1} = \frac{\alpha_{//} \sigma_{res}^x + \alpha_\perp \sigma_{res}^y}{\alpha_\perp \sigma_{res}^x + \alpha_{//} \sigma_{res}^y} \quad \text{[Math FIG. 7]}$$

If the denominator and the numerator of the equation 7 are divided by a $\alpha_\perp \sigma_{res}^x$ the same time, the equation 7 can be expressed as equation 8.

$$\frac{\Delta L_2}{\Delta L_1} = \frac{\frac{\alpha_{//}}{\alpha_\perp} + \frac{\sigma_{res}^y}{\sigma_{res}^x}}{1 + \frac{\alpha_{//}}{\alpha_\perp} \frac{\sigma_{res}^y}{\sigma_{res}^x}} = \frac{\frac{\alpha_{//}}{\alpha_\perp} + p}{1 + \frac{\alpha_{//}}{\alpha_\perp} p} \quad \text{[Math FIG. 8]}$$

$\alpha_\perp \alpha_{//}$ is referred as the conversion factor ratio. After the determination of the conversion factor ratio, the directionality of the residual stress can be determined by the indentation load difference from two indentations.

It is determined experimentally that the conversion factor ratio is constant, regardless of the types of materials or the indentation depth. Generally, the conversion factor is a variable affected by the indentation depth. However, it is determined experimentally that the ratio of $\alpha_\perp$ and $\alpha_{//}$ from the direction of the indentation with the Knoop indenter is constant.

2.2. Evaluation of Residual Stress

It is impossible to determine the residual stress of each axis through only the instrumented indentation test with the symmetric indenter, when the asymmetric biaxial residual stress exists. While the asymmetric biaxial residual stress operates on the surface deformation, the load change from the residual stress is transmitted to only one of the indented axes due to the symmetry of the indenter, regardless of the indenting direction.

If stress directionality or stress ratio p is determined, it's possible to evaluate the residual stress of each axis by equation 1. When equibiaxial (p=1) or uniaxial (p=0) residual stress states exist, it's possible to evaluate the residual stress by equation 1. However, because various subjects such as weldments, mechanical processing part or structural facility and so on except for the special case such as thin film includes the asymmetric biaxial residual stress, there has greatly high request to determine the stress directionality. Y. H. Lee et al. (Y. H. Lee, K. Takashima and D. Kwon: Scripta Mater., Vol. 50 (2004) p. 1193) performed the Rockwell indentation test and measured an impression shape of indentation by adopting a surface roughness tester, in order to confirm the pseduo-residual stress ratio. In this study, it is found that the stress-induced pile-up shift ratio on or near the biaxially measured impression of indentation is proportional to the residual stress ratio, as shown in FIG. 9.

There was the study to analyze an impression shape of indentation through an atomic force microscope in three dimensions and then predict the new stress factor and the stress directionality. However, in this study, it is possible to determine the stress directionality or stress ratio p by adopting the Knoop indentation test only two times. This method has a problem to perform the additional Knoop indentation test as well as the Vichers indentation test with the symmetric indenter.

The determination of the residual stress by adopting only the Knoop indentation test has been studied.

The summation of the load differences in equation 6 can be expressed as equation 9.

$$\Delta L_1 + \Delta L_2 = (\alpha_\perp + \alpha_{//})(\sigma_{res}^x + \sigma_{res}^y) \quad \text{[Math Figure 9]}$$

Here, $\alpha_\perp \alpha_{//}$ in equation 6 are conversion factors dependent on depth variables relating the residual stress to the indentation load difference, and $\alpha_\perp$, $\alpha_{//}$ are determined by the long diagonal direction of the Knoop indenter perpendicular and parallel to the direction of the indented residual stress. Therefore, $\alpha_\perp$, $\alpha_{//}$ at the given depth can be determined by the changing the amount of the residual stress. If the experimentally obtained conversion factors are added to equation 9, the sum of the residual stresses is obtained from the indentation load difference.

The equations 8 and 9 are expressed as the sum and the ratio of the residual stresses to get the equation 10.

$$\sigma_{res}^x + \sigma_{res}^y = \frac{\Delta L_1 + \Delta L_2}{\alpha_\perp + \alpha_{//}}$$ [Math FIG. 10]

$$p = \frac{\sigma_{res}^y}{\sigma_{res}^x} = \frac{\frac{\Delta L_2}{\Delta L_1} - \frac{\alpha_{//}}{\alpha_\perp}}{1 - \frac{\alpha_{//}}{\alpha_\perp} \frac{\Delta L_2}{\Delta L_1}}$$

$\alpha_\perp$, $\alpha_{//}$ are the experimentally determined values, while $\Delta L_1$ and $\Delta L_2$ are determined from the indentation load-depth curve. If the simultaneous equations in equation 10 are solved, the residual stress of each axis can be determined by only the Knoop indentation test.

FIG. 10 shows the procedures to solve the equations for the instrumented indentation test according to one embodiment of the present invention.

3. Experimental Procedures

The experiment is performed for evaluating the stress directionality p and the residual stress through the Knoop indentation test described in this specification.

The residual stress generator generates the biaxially applied residual stress to makes the symmetric/asymmetric stress states at first. And then the instrumented indentation test is performed to obtain the indentation load-depth curve according to the applied stress and the indenting direction. Finally, it is compared with the indentation load-depth curve in stress-free state.

The actual residue stress ratio and the residual stress of each axis are determined from the indentation load-depth curve change by adopting the above Knoop model. The conversion factor ratio is analyzed through the Finite Element Analysis. The introduction to the residual stress generator, the preparation of the specimen, the Knoop indenter, the applied instrumented indentation tester, the experimental procedures and the Finite Element Analysis are described as follows.

3.1. Residual Stress Generator

The new jig apparatus is invented for applying the asymmetric biaxial surfacial residual stress ($\sigma_{res}^x \neq \sigma_{res}^y \neq 0$, $\sigma_{res}^z = 0$) to a cruciform specimen, or a beam or rectangular specimen, as shown in FIGS. 11 and 12.

The newly invented jig apparatus includes the upper and the lower jigs on which grooves is formed respectively to support the cruciform specimen with 40×15×185 mm. The specimen is loaded inside grooves between the upper and the lower jigs and is fixed by a jig joining screw. The bending stress is induced by inserting a specimen bending screw into the screw hole of the upper and the lower jigs. Each of tensilely and compressively residual stress is applied to the center area of specimen by inserting a specimen bending screw into the indenting hole of the upper and the lower jigs. It is possible to control the amount of the applied stress by changing the inserting depth of the screw through the strain gauge located at the center area of the specimen. A curved supporting part is invented for strongly restricting the center area of the specimen so as to minimize out of plane deformation and at the same time smoothly transmitting the bending stress. Also, when the indentation load is applied to the center area of the bending deformed specimen, the jig joining screws are arranged by four and four on the inner and the outer sides of the upper and the lower jigs, and a rear specimen with 15 mm thick for minimizing the reduction of the generated residual stress.

3.2 Preparation of Specimen, Knoop Indenter and Instrumented Indentaion Tester 3.2.1. Applied Specimen and Preparation of Specimen The specimen in this study is API X65 steel and JIS S45C steel with a chemical components and mechanical properties in table 1. Because the latter steel has a good mechanical property, it is usually used for structural faculty and welding material. The above-described rectangular and cruciform specimens are machined and heat-treated in order to remove internal stress.

TABLE 1

| Materials | Chemical component (Fe bal.) | Elastic Modulus (GPa) | Poisson ratio | Yield strength (MPa) |
|---|---|---|---|---|
| API X-65 | 0.08% C, 0.019% P, 1.45% Mn, 0.003% S and 0.31% Si | 210 | 0.29 | 446 |
| ASTM A36 | 0.18% C, 0.019% P, 1.36% Mn, 0.003% S and 0.04% Si | 213 | 0.29 | 279 |
| JIS S45C | 0.45% C, 0.011% P, 0.07% Mn, 0.004% S and 0.03% Si | 214 | 0.29 | 348 |

Heat-treatment at an appropriate temperature below $A_1$ for removing the residual stress generated from forge, casting, machining and welding, is regarded as a stress relief annealing. If the steer part with the residuary residual stress is used as it is, the time elapse may reduce the stress so as to let its size and shape change. If a piece of that is cut by machining, the internal stress of the material can't keep its equilibrium, so that it is changed into its new equilibrium to become deformed. For preventing this deformation, it needs to sufficiently remove the residual stress by heating material at an appropriate temperature. Usually it is performed above recrystallization temperature (450° C.) below deformation point $A_1$. This temperature is maintained for one hour per 25 mm thick and then a slowly cooling is performed at 200° C./h.

Generally speaking, as the heating temperature is higher, so the material is softer experiment plastic deformation by the residual stress happens and the stress is reduced gradually and then removed completely. As carbon content of carbon steel is more, so the residual stress is more and it's hard to remove it.

Full annealing or normalizing is performed for refine of crystallization grain and the control of structure together with the residual stress relief.

In this experiment, API X-65 keeps 600° C. during about two hours and another material does during about one hour, and then slowly cooling is performed. After the residual stress relief by heat treatment, the yield strength, the modulus of elasticity and the poisson ratio is obtained from the indentation test and the ultrasonic wave speed analysis. The surface is grinded with a sandpaper 100, 200, 400, 600, 800, 1000 or 1500 times for the instrumented indentation test and the attachment of a strain gauge.

3.2.2 Knoop Indenter and Instrument Indentation Tester

The previous asymmetric Knoop indenter with 7.11:1 as shown in FIG. 13 is used for evaluating the asymmetry of the material, which comes from a phenomenon where the length of the long diagonal is changed according to the crystal direction of the material. Evaluating the asymmetry of the material is converted into the hardness so as to obtain the relationship with the crystal direction of the material. There is the previous study to suggest the relationship with the residual stress through the Knoop indenter hardness as shown in FIG. 8.

The optical observation of the impression shape has a lot of errors and obtains the residual stress through the hardness by only the plasticity so that it is hard to directly apply to the evaluation of the residual stress. Because the previous Knoop indenter has been applied to the small-scaled areas, the indentation load below 6 kgf does not distort the impression shape and a resolution of a load cell causes the incorrect experimental value.

In this specification, the Knoop indenter is manufactured with the geographically identical Knoop indenter shape and consists of diamond, which can apply to the indentation load to the macro scales arrange of above 100 kgf. The applied instrumented indentation equipment is Frontics Inc.'s AIS3000(maximum load: 300 kgf, load resolution: 5.6 gf, variable resolution: 0.1 μm). This equipment synchronizes the load measured by the load cell with the variable signal measured by the variable sensor so as to generate the indentation load-depth curve. The indenter holder and the instrumented indentation equipment are manufactured as one body in order to minimize the compliance effect for an equipment, as shown in FIG. 14. FIG. 15 shows the measured values of the Knoop indenter of FIG. 14. FIG. 16 is the photograph of the instrumented indentation equipment applied to one embodiment of the present invention.

3.3 Experimental Procedure 3.3.1. Determination of Optimized Experimental Conditions There needs to determine various experimental conditions before the instrumented indentation equipment is applied. The important factors to the experimental value are divided into two parts.

The first is the experimental variable to affect the revival of the indentation load-depth curve as the basic data of the instrumented indentation test. This factor may be one or more of the indentation speed, the surface roughness and the indentation depth and so on. When there are less than 10 of crystal grains inside the indented surface, not the average deformation properties of the material but the individual properties of crystal grains inducing the deformation are obtained from the test. As shown in FIG. 17, when the spherical indenter indents an API X-65 material at the maximum 150 μm, and the average size of grains is 10 μm, there are about tens thousand grains within plastic zone and millions grains within elastic zone. This specification determined that the optimized indentation depth is 100 μm because of the better revival from the repeated experiment at various depth. For knowing the relationship between the surface roughness and the indentation speed, the standard deviations at indentation depth of 20, 40, 60, 80, 100 μm are compared with each other when the indentation speeds are changed at various roughness. The grind condition of the surface and the indentation speed of 0.1 mm/min is based on the result of FIG. 18.

The second is the analysis method as the most important factor. In this specification, the difference between load at stress-free state and load where the residual stress is applied is analyzed per each depth of 10 μm from 20 μm to 100 μm except for the initial depth.

3.3.2. Experimental Procedure

The experimental procedure to obtain the indentation load-depth curve at stress-free state for each specimen before the residual stress is applied is as follows. A cruciform specimen or a rectangular specimen is equipped with the residual stress generator in FIG. 11 and then the instrumented indentation test is applied with the indenting hole located at the center of the upper jig. There is indented to the indentation depth of 100 μm by 0.1 mm/min, And then the load is removed to 70% of load relief rate. Zero index is setup as 1 kg. When zero index for the indenter with elongated four-sided pyramidal geometry is setup as 0.06 kg, nonlinear range may occur. Therefore, the initial contact load is determined as 1 kgf. The experiment is repeated three times according to each axis of the indenting directions. There is indented with a distance interval of 3 mm between the impression shapes in order to prevent overlapping the plastic zone of each other.

After the indentation load-depth curve is obtain at stress-free state, the biaxial strain gauge is attached on the surface of specimen and the elastic deformation ratio is obtained from the strain gauge by rotating the specimen bending screw. The elastic deformation ratio is exchanged with the residual stress of each axis through equation 11.

$$\sigma_{res}^x = \frac{E}{(1-v^2)}(\varepsilon_x + v\varepsilon_y),$$ [Math FIG. 11]

$$\sigma_{res}^y = \frac{E}{(1-v^2)}(\varepsilon_y + v\varepsilon_x)$$

The residual stress is applied within the elastic limit by using Tresca yield condition.

There gradually increases a bend strain by about 50με on both sides of the specimen in order to prevent the distortion of the asymmetric specimen until the strain is attained to the designated values. The instrumented indentation test is applied at the same condition as the indentation test of stress-free state.

When the indentation curves from the instrumented indentation test are overlapped with each other, the curve at the center area is selected as the curve representing each stress state and then analyzed. When the axis to which the stress-free state and the largest residual stress is added is regarded as the x axis, the long diagonal of Knoop indenter is perpendicular to the x-axis and the y-axis to obtain the indentation load-depth curve and then $\Delta L_1$ and $\Delta L_2$ are determined as the load differences obtained from each of depths through that.

3.3.3 Proof for Direct Summation

As described in 2.1 section, the experiment shown in FIG. 6 is performed to prove the assumption that the effect of the residual stress of each different on the indentation load can be expressed in the form of the summation. The sum of the indentaion load difference in that the long diagonal of the indenter is perpendicular and parallel to the direction of the uniaxially applied residual stress of 200 MPa is compared with the load difference of the biaxially applied residual stress of 200 MPa.

3.3.4 Determination of Conversion Factor Ratio

First of all, the conversion factor should be determined for getting the conversion factor ratio. The conversion factor $\alpha_\perp$, $\alpha_{//}$ in equation 6 are the constant determined by the indentation depth and associated between the residual stress and the induced load from the residual stress when the residual stress is uniaxially applied and the direction of the residual stress is perpendicular or parallel to the direction of the indentation with the Knoop indenter. There can determine $\alpha_\perp$ or $\alpha_{//}$ at each depth along with changing the amount of the residual stress.

FIG. 19 is a mimetic diagram of the applied experiment for determining the conversion factor. There can determine the residual stress and the anisotropic factor of that from the ratio and the sum of conversion factors at each depth.

3.3.5. Proof for Modeling

After the residual stress with a biaxial tension including a uniaxial that is applied and the Knoop indenter is indented to the direction parallel to each axis, the anisotropic factor of the residual stress is determined by using the load difference and the load ratio. The result is compared with the actual residual stress ratio. The sum of the residual stress is determined from the sum of the load difference and gives the residual stress of each axis from solving simultaneous equations with the residual stress ratio. The residual stress is compared with the actual residual stress applied at each axis.

4. Finite Element Analysis

The input file is generated by MSC. Patran in order to perform the computer mimitation of the Knoop indentation test and the finite element analysis is performed by ABAQUS finite element code. The geographic shape of the Knoop indenter has 2-fold symmetry to perform the modeling by ¼ of all specimens. The 3-D specimen is constructed by 32,160 of 8-node brick element. The reduced integration is introduced in order to reduce the computing time. The von Mises yield condition is applied for the finite element analysis.

The bottom surface of the specimen is fixed to the axial direction and the symmetry boundary condition is applied across the centric surface. It is supposed that the indenter has a rigid body and the specimen may be plastic. The API X-65 is applied to the finite element analysis of the instrumented indentation test. The plastic movement uses the measured modulus of elasticity in 3.2.1 section, the yield strength and the poisson ratio, while the plastic movement is modeled by using the tension curve of the material which is obtained from the uniaxial tension test.

Various kinds of the residual stresses are applied by making a homogeneous stress field at both sides of the specimen. The maximum indentation depth is 120 µm and the computer mimitation of the Knoop indentation test is performed by controlling the indentation depth.

5. Result and Discussion

After the residual stress with equi and non-equi biaxial tensions including an uniaxial is applied, the indentation load-depth curves when the long diagonal of the Knoop indenter is perpendicular to either x or y axes are referred as $L_1$ and $L_2$, respectively.

FIGS. 20 to 22 show the results when they are overlapped with the curve in stress-free state. These results also show that all indentation loads of the applied specimen in this specification are 100 kgf when the indented depth is 100 µm. These results show that when the residual stresses of stress-free and equi-biaxial states are applied, the indentation load-depth curves are constant without the indenting direction. It may be known that what the change of hardness happens according to the indenting direction of the Knoop indenter in either the micro-hardness test or the nano-indentation test means that the effect on the crystallized direction of the material is great.

In this specification, because of the relatively deep indentation, a lot of the crystallization grains are contained beneath the indenter, which causes the same effect as the indentation of the isotropic material. It is possible to consider the asymmetry of the material except for the effect of the crystallized direction of the material. It is confirmed that there is no problem for performing the modeling in this specification to the macro scale. However, the crystallized direction of the material to the nano or micro scale should be considered. Because the biaxial residual stress is considered in this specification, the effect of the indenting direction on "out of plane residual stress" does not appear. Therefore, there needs the study including the effect of the indenting direction on "out of plane residual stress" and the modeling including the effect of the crystallized asymmetry to apply to the thin film and the micro-scaled material.

This section describes the determination of the conversion factor and the proof for the Knoop modeling. It is shown that the conversion factor ratio is related to the asymmetry of the indenter through the finite element analysis.

5.1. Determination of Conversion Factor Ratio

First of all, the conversion factor should be determined for getting the conversion factor ratio. The conversion factor $\alpha_\perp$ and $\alpha_{//}$ in equation 6 are the constant determined by the indentation depth and associated between the residual stress and the induced load induced from the residual stress when the residual stress is uniaxially applied and the direction of the residual stress is perpendicular or parallel to the direction of the indentation with the Knoop indenter. There can determine $\alpha_\perp$ or $\alpha_{//}$ at each depth along with changing the amount of the residual stress.

FIG. 23 includes the graphs to linearly connect the load differences with the starting point of coordinate when the uniaxial residual stresses of 208, 389 MPa are applied. Only one line with the above three points is determined. What this fitted line is similar to the straight line is the same as the previous study by Vicker indenter, which means that the load difference is generated relative to the residual stress.

FIG. 24 draws the conversion factors $\alpha_\perp$, $\alpha_{//}$ according to the indentation depth. As shown in FIG. 24, the conversion factors $\alpha_\perp$, $\alpha_{//}$ tend to be increased as the indentation depth become larger. What the conversion factors at each depth are directly determined and then the conversion factor ratio is determined as their ratio, is referred as a forward method.

The conversion factor ratio can be determined from the indentation load difference ratio. As p=0 for the uniaxial state, equation 8 may be expressed as equation 12.

$$\frac{\Delta L_2}{\Delta L_1} = \frac{\frac{\alpha_{//}}{\alpha_\perp} + p}{1 + \frac{\alpha_{//}}{\alpha_\perp} p} = \frac{\alpha_{//}}{\alpha_\perp} \qquad \text{[Math FIG. 12]}$$

This method is referred as a reverse method. As both values from forward and reverse methods are compared with each other, so the proposed direct summation is confirmed and the validity of this modeling is proved. If the conversion factors are determined regarding the indenting direction and their ratio is equal to the value from equation 12 by modeling, the direct summation must be proved.

FIGS. 25 and 26 show the conversion factor ratios for API X-65. FIGS. 27 and 28 show the conversion factor ratios for ASTM A35. FIGS. 29 and 30 show the conversion factor ratios for JIS S45C. FIG. 31 comparatively show the conversion factor ratios for the above three steels at each depth at the same time. It is found in FIG. 32 that the conversion factor ratios tend to be about 0.34 regardless of the indentation depth.

However, the conversion factor ratios by the forward method of API X-65 and ASTM A36 are about 0.35 and 0.31, respectively. As they are regarded as an experimental error, the relationship between the amount of the residual stress and the load difference is analyzed by the data from each material.

As shown in FIG. 32, it is found that the indentation load difference is generated relative to the amount of the residual stress regardless of the material. It is determined from this result that the conversion factor ratio is 0.34. Although only three kinds of steels are related with the above result, six kinds of the residual stresses are applied and it is found that this result is proportional to the amount of them. As their ratio is constant regardless of indentation depth, it is determined that the conversion factor ratio is a variable to relate the Knoop indenter to the biaxial residual stress.

As described in 5.3 section, it is proved through the finite element analysis that the conversion factor ratio is a function of the asymmetry of the indenter. It is confirmed in this specification that the indentation load difference is generated relative to the residual stress of each axis and the indentation load difference of each axis in the biaxial state can be expressed in the form of the summation.

5.2 Proof for the Knoop Modeling

To prove the above described Knoop modeling, after the residual stress with the uniaxial tension is applied by the residual stress generator, the instrumented indentation test is applied to each axis with the applied residual stress, parallel to the long diagonal direction of the Knoop indenter. As $\Delta L_1$ and $\Delta L_2$ from the instrumented indentation test is substituted for equation 13, the asymmetry coefficient of the residual stress and the residual stress of each axis may be calculated.

$$\sigma_{res}^x + \sigma_{res}^y = \frac{\Delta L_1 + \Delta L_2}{\alpha_\perp + \alpha_{//}} \quad \text{[Math FIG. 13]}$$

$$p = \frac{\sigma_{res}^y}{\sigma_{res}^x} = \frac{\frac{\Delta L_2}{\Delta L_1} - 0.34}{1 - 0.34\frac{\Delta L_2}{\Delta L_1}}$$

If the asymmetry coefficient of the residual stress is compared with the actual residual stress, the residual stress of each axis is compared with the actual residual stress.

5.2.1. Determination of Asymmetry Coefficient of Residual Stress

It is confirmed that the result of the actual modeling through the conversion factor ratio (p=0.34) is substantially equal to the experimental result. FIG. 33 show that the indentation load difference from the instrumented indentation test for API X-65 is compared with the actual residual stress p when various kinds of residual stresses are applied. The function fitted by equation 14 is equal to this indentation result, which means that the Knoop modeling is valid.

$$p = \frac{\sigma_{res}^y}{\sigma_{res}^x} = \frac{\frac{\Delta L_2}{\Delta L_1} - 0.34}{1 - 0.34\frac{\Delta L_2}{\Delta L_1}} \quad \text{[Math FIG. 14]}$$

FIG. 34 shows the ratio of the indentation load difference from the instrumented indentation test to the actual residual stress after the residual stress with the biaxial tension is applied to the three kinds of steels in this specification. It is found that the asymmetry coefficient p of the residual stress is determined from the indentation load difference.

5.2.2. Determination of Residual Stress

FIG. 35 is the graph to show the sum of the conversion factors, $\alpha_\perp$, $\alpha_{//}$ according to indentation depth. The sum of the conversion factor per each depth can be calculated to the sum of the residual stresses through equation 15.

$$\sigma_{res}^x + \sigma_{res}^y = \frac{\Delta L_1 + \Delta L_2}{\alpha_\perp + \alpha_{//}} \quad \text{[Math FIG. 15]}$$

If the simultaneous equations in equation 14 and 15 are solved, the ratio and the sum of the residual stresses may be changed into the residual stress of each axis. As an example, it shows the result of the residual stress when the residual stress with uni-axial tension of 208 MPa is applied. FIG. 36 shows the result of the Knoop indentation test for the API X-65 cruciform specimen to which the residual stress with uni-axial tension of 208 MPa is applied. The sum of the indentation load differences is induced from the indentation load differences $\Delta L_1$ and $\Delta L_2$. If the simultaneous equations in equation 14 and 15 are solved, the ratio and the sum of the residual stresses may be changed into the residual stress of each axis, which is shown in the table 2. FIG. 37 shows the calculated residual stresses from the above procedure.

TABLE 2

|  | $\Delta L_1 + \Delta L_2$ | $\sigma_{res}^x + \sigma_{res}^y$ | $\sigma_{res}^x$ | $\sigma_{res}^y$ |
| --- | --- | --- | --- | --- |
| 20 | 0.388877 | 167.6766 | 170.1177 | −2.44119 |
| 30 | 0.820807 | 198.2626 | 201.1491 | −2.88649 |
| 40 | 1.404737 | 213.8108 | 216.9237 | −3.11285 |
| 50 | 2.140667 | 218.8821 | 222.0688 | −3.18669 |
| 60 | 3.028597 | 221.5506 | 224.7762 | −3.22554 |
| 70 | 4.068527 | 232.4873 | 235.872 | −3.38476 |
| 80 | 5.260458 | 237.4924 | 240.9501 | −3.45763 |
| 90 | 6.604388 | 242.7191 | 246.2529 | −3.53373 |
| 100 | 8.100318 | 247.7919 | 251.3995 | −3.60758 |
| AVG. | 3.535264 | 220.0748 | 223.2789 | −3.20405 |

However, as the sum of the residual stresses is induced from the sum of the conversion factors according to the indentation depth, the change of the indentation depth may affect the amount of the finally decided residual stress. As the ratio of the residual stresses is determined from the conversion factor ratio which is constant regardless of the indentation depth, it has constant value regardless of the indentation depth. Consequently, the determination of the residual stress leads to the research against the physical meaning of following conversion factor.

5.3. Research Against the Physical Meaning of Following Conversion Factor

Suppose that the previous calculated conversion factor ratio is the function of the asymmetry for the knoop indenter. The symmetric indenter such as the vickers indenter produces only one indentation load-depth curve in various residual stresses regardless of the indenting direction and the indentation load difference is proportional to the average amount of residual stress. However, The asymmetric Knoop indenter with asymmetry axis length ratio of 7.11:1 produces the different indentation load-depth curve in various residual stresses regarding the indenting direction. In special, when the longer diagonal of the knoop indenter is perpendicular or parallel to the applied direction of the residual stress with the largest tension, the indentation load tends to be relatively either the smallest or the largest. As the asymmetry is larger, so it may be reflected of its effect on a large scale, as shown in FIG. 38.

The modified Knoop indentation test is applied by the ABAQUS program. FIG. 39 shows that the experimental result when the Knoop indenter is indented on API X-65 of stress-free state is compared with that obtained by using the FEA. It is proved that the FEA is valid because the experimental result is equal to that from the FEA. FIG. 40 show the result from the computer mimitation after the biaxial residual stress equal to the actual experimental value is applied. It is shown that the result is matched with the fitted line with the Knoop modeling in 5.2.1 section.

FIG. 41 shows the result from the FEA in residual stress states with various biaxial tensions (p=0, 0.25, 0.5, 1) when the ratios of long and short diagonal lengths in the asymmetric indenter are a 3.5:1 and 14.1. When the ratio of long and short diagonal lengths in the asymmetric indenter are a 3.5:1, the conversion factor ratio is 0.63 higher than 0.34 in the actual Knoop indenter. In contrast, when the ratio of long and short diagonal lengths in the asymmetric indenter is 14.1, the conversion factor ratio is 0.14. As the asymmetry is larger than the Knoop indenter, so it is found that the conversion factor ratio approaches with 0 and that the ratio of the indentation load difference when indented by the indenter with the knife blade is the same as the ratio of the actual residual stress.

This result shows that the conversion factor ratio is the constant which is decided by the asymmetry of the indener and the higher asymmetry leads to the effect of only one axis on the residual stress. In contrast, if the indener reaches the symmetry, so the conversion factor ratio reaches 1. Therefore, the conversion factor ratio may be the function of the asymmetry of the indenter. In this specification, the FEA is performed with Knoop indenter with 3.5:1 and 14:1 and only the tendency is observed. It is expected that the studies about the geometry of the indenter and the conversion factor ratio will appear soon.

INDUSTRIAL APPLICABILITY

6. Result

The directionality of biaxial residual stress and the residual stress for each axis were determined by using non-equi indenter such as the Knoop indenter. The previous study needed to determine the directionality (p) of residual stress in order to evaluate the residual stress by using the symmetric indenter. However it's possible to determine the directionality of biaxial residual stress and the residual stress for each axis using the asymmetric indenter in this specification.

1. After the residual stress with a biaxial tension including a uniaxial that is applied, the Knoop indentation test is made. The slope of indentation load-depth curve when the long diagonal of Knoop indenter is perpendicular to the direction to which the largest residual stress is applied, is the lowest value, compared with that in stress-free state. Also, the slope of indentation load-depth curve when the long diagonal of Knoop indenter is parallel to the direction to which the largest residual stress is applied, is the highest, compared with that in stress-free state.

2. Due to the asymmetry of the Knoop indenter with elongated geometry of which has a 7.11:1 for long and short diagonal lengths, it is determined experimentally that the load difference from the residual stress is changed regarding the indenting direction. The Knoop modeling was performed by modifying the previous Veckers modeling based on the above result.

It is proved mathematically and found experimentally that the indentation load difference in the biaxial residual stress state is induced from the conversion factor ($\alpha_\perp$, $\alpha_{//}$) which connects the residual stress with the indentation load difference from the residual stress regarding the uniaxial residual stress and the long diagonal direction of the Knoop indenter.

3. When the Knoop indenter, of which the long diagonal direction is parallel or perpendicular to the direction of the largest residual stress, is indented, the applied load differences ($\Delta L_1$, $\Delta L_2$) and their ratio may be expressed as the function of the conversion factor ratio ($\alpha_\perp$, $\alpha_{//}$) and the actual residual stress ratio (p). As various tensile residual stresses are uniaxially applied to three kinds of steels and the ratio of the conversion factor ($\alpha_\perp$, $\alpha_{//}$) is determined, so the asymmetry of the residual stress may be determined from the indentation load difference ratio.

4. It was experimentally determined that the conversion factor ratio ($\alpha_\perp$, $\alpha_{//}$) is the constant value 0.34 regardless of the kind of the material and the indenting depth. After the residual stress with various biaxial tension is applied to the three kinds of steels and then the Knoop indentation test is performed for them, the directionality of the residual stress is determined through the Knoop modeling. Also, it was mathematically found that the sum of the conversion factor ratio ($\alpha_\perp$, $\alpha_{//}$) is proportional to the sum of the residual stress and the residual stress of each axis is determined from the previously determined residual stress ratio.

5. It's confirmed that the conversion factor ($\alpha_\perp$, $\alpha_{//}$) is the factor related to the geographical shape of the indenter. As the asymmetry of the indenter is larger, so it is supposed that the conversion factor ratio reaches with 0 and that the ratio of the indentation load difference is the same as the ratio of the actual residual stress. However, the FEA was performed by using two modified Knoops ((14:1, 3.5:1) and the above assumptions for the experiment is proved to be valid.

6. There has the problem to determine the indentation load-depth curve in stress-free state at the actual application. Also, other problem is to determine the direction of the main residual stress. Basically, because the evaluation of the residual stress from the instrumented indentation test is that the residual stress is quantitatively induced through the indentation load difference from the residual stress at the same depth, with being overlapped with the indentation load-depth curve in stress-free state, it is inevitable to determine the indentation load-depth curve in the stress-free state.

In order to solve this problem, there is the research in which the indentation load-depth curve in the stress-free state is also determined through the FEA recently. Finally, it is very hard to determine the direction of main residual stress except for the welding part. The direction of main residual stress for the welding part may be determined in reference to the welding line. Therefore, There is the research in which the indentation test is performed four times with the Knoop indenter rotated by 45° and then the stresses are obtained from the indentation load difference, the amount of main stress is determined from the relation with stresses and the direction of main stress.

Although embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A method for evaluating an asymmetric residual stress for a material by an indentation test, the method comprising:
applying residual stresses with uniaxial and symmetrical biaxial tensions on the material and then performing an instrumented indentation test indenting an asymmetric indenter on the material; and
comparing a slope of indentation load-depth curve when the long diagonal direction of the asymmetric indenter is perpendicular to the direction of the largest residual stress with that in stress-free state, and then a slope of indentation load-depth curve when the long diagonal direction of the asymmetric indenter is parallel to the direction of the largest residual stress with that in stress-free state, so as to evaluate the asymmetric residual stress for the material.

2. The method in claim 1, wherein the asymmetric indenter has geometry of 7.11:1 for long and short diagonal lengths.

3. The method in claim 1, further comprising:
determining a ratio of the conversion factor $(\alpha_\perp, \alpha_{//})$ which associates the residual stress with the induced indentation load difference from the residual stress according to the uniaxial residual stress and the longer diagonal direction of the asymmetric indenter; and
using the conversion factor ratio and the ratio of the induced indentation load differences ($\Delta L_1$ and $\Delta L_2$) when the long diagonal direction of the asymmetric indenter in the biaxial residual stress state is perpendicular or parallel to the direction of the largest residual stress, then to determine the stress directionality (p).

4. The method in claim 3, wherein the conversion factor ratio is 0.34.

5. The method in claim 4, wherein the stress directionality (p) is determined by the formula below with the conversion factor ratio and the indentation load difference ratio:

$$\frac{\Delta L_2}{\Delta L_1} = \frac{\frac{\alpha_{//}}{\alpha_\perp} + \frac{\sigma^y_{res}}{\sigma^x_{res}}}{1 + \frac{\alpha_{//}}{\alpha_\perp}\frac{\sigma^y_{res}}{\sigma^x_{res}}} = \frac{\frac{\alpha_{//}}{\alpha_\perp} + p}{1 + \frac{\alpha_{//}}{\alpha_\perp}p}.$$

6. The method in claim 5, further comprising:
solving the simultaneous equations in the formula below which contains the conversion factor, and the ratio and the sum of the residual stress, and determining the residual stress of both of the longer and shorter diagonals:

$$p = \frac{\sigma^y_{res}}{\sigma^x_{res}} = \frac{\frac{\Delta L_2}{\Delta L_1} - 0.34}{1 - 0.34\frac{\Delta L_2}{\Delta L_1}}$$

$$\sigma^x_{res} + \sigma^y_{res} = \frac{\Delta L_1 + \Delta L_2}{\alpha_\perp + \alpha_{//}}.$$

7. The method in claim 6, further comprising:
confirming a relationship between the geometry of the asymmetric indenter and the conversion factor ratio through Finite Element Analysis.

8. A non-transitory computer-readable medium storing a program for execution on a computer processor, the program comprising steps of the method for evaluating an asymmetric residual stress for a material by the indentation test in claim 1.

9. An instrumented indentation apparatus for applying an instrumented indentation test by executing a computer-readable medium comprising a program for execution on a computing device, wherein the program comprises steps of the method for evaluating an asymmetric residual stress for a material by the indentation test in claim 1.

10. A non-transitory computer-readable medium storing a program for execution on a computer processor, the program comprising steps of the method for evaluating an asymmetric residual stress for a material by the indentation test in claim 2.

11. A non-transitory computer-readable medium storing program for execution on a computer processor, the program comprising steps of the method for evaluating an asymmetric residual stress for a material by the indentation test in claim 3.

12. A non-transitory computer-readable medium storing a program for execution on a computer processor, the program comprising steps of the method for evaluating an asymmetric residual stress for a material by the indentation test in claim 4.

13. A non-transitory computer-readable medium storing a program for execution on a computer processor, the program comprising steps of the method for evaluating an asymmetric residual stress for a material by the indentation test in claim 5.

14. A non-transitory computer-readable medium storing a program for execution on a computer processor, the program comprising steps of the method for evaluating an asymmetric residual stress for a material by the indentation test in claim 6.

15. A non-transitory computer-readable medium storing a program for execution on a computer processor, the program comprising steps of the method for evaluating an asymmetric residual stress for a material by the indentation test in claim 7.

16. An instrumented indentation apparatus for applying an instrumented indentation test by executing a computer-readable medium comprising a program for execution on a computing device, the program comprising steps of the method for evaluating an asymmetric residual stress for a material by the indentation test in claim 2.

17. An instrumented indentation apparatus for applying an instrumented indentation test by executing a computer-readable medium comprising a program for execution on a computing device, the program comprising steps of the method for evaluating an asymmetric residual stress for a material by the indentation test in claim 3.

18. An instrumented indentation apparatus for applying an instrumented indentation test by executing a computer-readable medium comprising a program for execution on a computing device, the program comprising steps of the method for evaluating an asymmetric residual stress for a material by the indentation test in claim 4.

19. An instrumented indentation apparatus for applying an instrumented indentation test by executing a computer-readable medium comprising a program for execution on a computing device, the program comprising steps of the method for evaluating an asymmetric residual stress for a material by the indentation test in claim 5.

20. An instrumented indentation apparatus for applying an instrumented indentation test by executing a computer-readable medium comprising a program for execution on a computing device, the program comprising steps of the method for evaluating an asymmetric residual stress for a material by the indentation test in claim 6.

21. An instrumented indentation apparatus for applying an instrumented indentation test by executing a computer-readable medium comprising a program for execution on a computing device, the program comprising steps of the method for evaluating an asymmetric residual stress for a material by the indentation test in claim 7.

* * * * *